US006241288B1

(12) United States Patent
Bergenek et al.

(10) Patent No.: US 6,241,288 B1
(45) Date of Patent: *Jun. 5, 2001

(54) FINGERPRINT IDENTIFICATION/VERIFICATION SYSTEM

(75) Inventors: Jerker Bergenek; Christer Fåhraeus, both of Lund; Linus Wiebe; Mårten Öbrink, both of Malmö, all of (SE)

(73) Assignee: Precise Biometrics AB (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/128,442

(22) Filed: Aug. 3, 1998

Related U.S. Application Data

(60) Provisional application No. 60/080,430, filed on Apr. 2, 1998.

(51) Int. Cl.[7] .................................................. B42D 15/00
(52) U.S. Cl. ................... 283/67; 283/69; 283/78; 382/116; 382/124; 396/15
(58) Field of Search .................... 283/67, 68, 69, 283/78; 382/116, 124; 396/15

(56) References Cited

U.S. PATENT DOCUMENTS

| 4,541,113 | * | 9/1985 | Seufert et al. ........................ 382/4 |
| 4,582,985 | | 4/1986 | Löfberg . |
| 4,607,384 | * | 8/1986 | Brooks .................................. 382/4 |
| 4,641,350 | * | 2/1987 | Bunn .................................... 382/4 |
| 4,669,753 | * | 6/1987 | Land et al. .......................... 283/1 A |
| 4,790,564 | * | 12/1988 | Larcher et al. ....................... 283/69 |
| 5,140,642 | * | 8/1992 | Hsu et al. .............................. 382/5 |
| 5,291,560 | | 3/1994 | Daugman . |
| 5,493,621 | | 2/1996 | Matsumura . |
| 5,509,083 | | 4/1996 | Abtahi et al. . |
| 5,555,314 | | 9/1996 | Nakajima . |
| 5,572,597 | | 11/1996 | Chang et al. . |
| 5,623,552 | | 4/1997 | Lane . |
| 5,845,005 | * | 12/1998 | Setlak et al. ....................... 382/124 |
| 5,901,239 | * | 5/1999 | Kamei ................................ 382/125 |
| 5,909,501 | * | 6/1999 | Thebaud ............................. 382/124 |

FOREIGN PATENT DOCUMENTS

| 0855667 | 7/1998 | (EP) . |
| WO9852149 | 11/1998 | (WO) . |

OTHER PUBLICATIONS

C. L. Wilson, G. T. Candela, and C. I. Watson, Neural–Network Fingerprint Classification, Journal of Artificial Neural Networks, vol. 1 (2) (1994): pp. 203–228.

(List continued on next page.)

Primary Examiner—A. L. Wellington
Assistant Examiner—Monica S. Carter
(74) Attorney, Agent, or Firm—Cooper & Dunham LLP

(57) ABSTRACT

A fingerprint identification/verification system using bitmaps of a stored fingerprint to correlate with a bitmap of an input fingerprint, wherein an accurate reference point is located and selected two-dimensional areas in the vicinity of the reference point of the input image of the fingerprint are correlated with stored fingerprint recognition information to determine if the input fingerprint image and the stored fingerprint recognition information are sufficiently similar to identify/verify the input fingerprint.

31 Claims, 27 Drawing Sheets

OTHER PUBLICATIONS

H. C. Lee and R. E. Gaensslen, eds. Advances In Fingerprint Technology, CRC Press (Sep. 1992): pp. 48–53.

V. S. Srinivasan and N. N. Murthy, Detection of Singular Points in Fingerprint Images, Pattern Recognition, vol. 125, No. 2, (1992): pp. 139–153.

D. K. Isenor and S. G. Zaky, Fingerprint Identification Using Graph Matching, Pattern Recognition, vol. 19, No. 2, (1986): pp. 113–122.

C. H. Lin et al., Fingerprint Comparison 1: Similarity of Fingerprints, Journal of Forensic Sciences, JFSCA, vol. 27, No. 2, (1982): pp. 290–304.

C. V. Kameswara Rao and K. Balck, Finding The Core Point In A Fingerprint, IEEE Transcation On Computers, vol. C–27, No. 1, (Jan. 1978): pp. 77–81.

* cited by examiner

— RIDGE ENDING
— BIFURCATION
— LAKE
— INDEPENDENT RIDGE
— DOT OR ISLAND
— SPUR
— CROSSOVER $$\begin{bmatrix} 7 & 0 & 8 & 0 & 1 & 0 & 2 & 0 & 3 \\ 0 & 0 & 0 & 0 & 0 & 0 & 0 & 0 & 0 \\ 6 & 0 & 7 & 8 & 1 & 2 & 3 & 0 & 4 \\ 0 & 0 & 6 & 0 & 0 & 0 & 4 & 0 & 0 \\ 5 & 0 & 5 & 0 & C & 0 & 5 & 0 & 5 \\ 0 & 0 & 4 & 0 & 0 & 0 & 6 & 0 & 0 \\ 4 & 0 & 3 & 2 & 1 & 8 & 7 & 0 & 6 \\ 0 & 0 & 0 & 0 & 0 & 0 & 0 & 0 & 0 \\ 3 & 0 & 2 & 0 & 1 & 0 & 8 & 0 & 7 \end{bmatrix}$$

Fig. 30

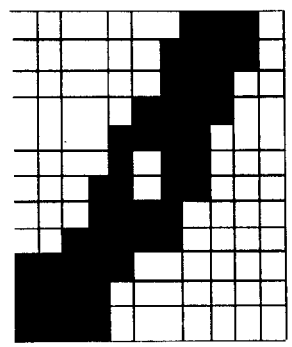

Fig. 31

$$\begin{bmatrix} 7 & 0 & 0 & 8 & 0 & 0 & 1 & 0 & 0 & 2 & 0 & 0 & 3 \\ 0 & 0 & 0 & 0 & 0 & 0 & 0 & 0 & 0 & 0 & 0 & 0 & 0 \\ 0 & 0 & 7 & 0 & 8 & 0 & 1 & 0 & 2 & 0 & 3 & 0 & 0 \\ 6 & 0 & 0 & 0 & 0 & 0 & 0 & 0 & 0 & 0 & 0 & 0 & 4 \\ 0 & 0 & 6 & 0 & 7 & 8 & 1 & 2 & 3 & 0 & 4 & 0 & 0 \\ 0 & 0 & 0 & 0 & 6 & 0 & 0 & 0 & 4 & 0 & 0 & 0 & 0 \\ 5 & 0 & 5 & 0 & 5 & 0 & C & 0 & 5 & 0 & 5 & 0 & 5 \\ 0 & 0 & 0 & 0 & 4 & 0 & 0 & 0 & 6 & 0 & 0 & 0 & 0 \\ 0 & 0 & 4 & 0 & 3 & 2 & 1 & 8 & 7 & 0 & 6 & 0 & 0 \\ 4 & 0 & 0 & 0 & 0 & 0 & 0 & 0 & 0 & 0 & 0 & 0 & 6 \\ 0 & 0 & 3 & 0 & 2 & 0 & 1 & 0 & 8 & 0 & 7 & 0 & 0 \\ 0 & 0 & 0 & 0 & 0 & 0 & 0 & 0 & 0 & 0 & 0 & 0 & 0 \\ 3 & 0 & 0 & 2 & 0 & 0 & 1 & 0 & 0 & 8 & 0 & 0 & 7 \end{bmatrix}$$

Fig. 32

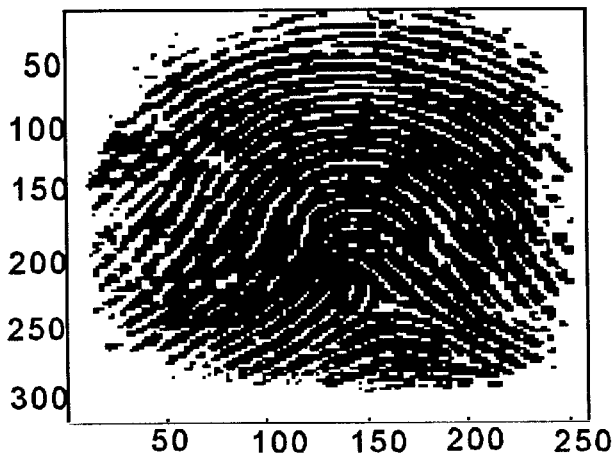

Fig. 33

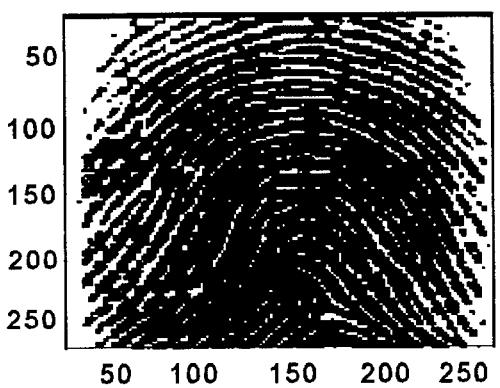
Fig. 34
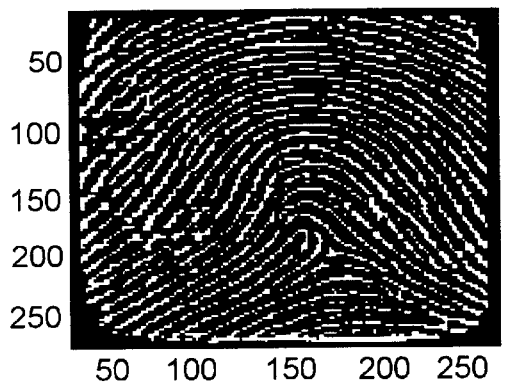 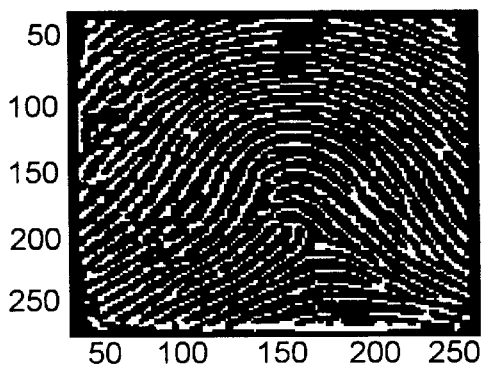
Fig. 35     Fig. 36
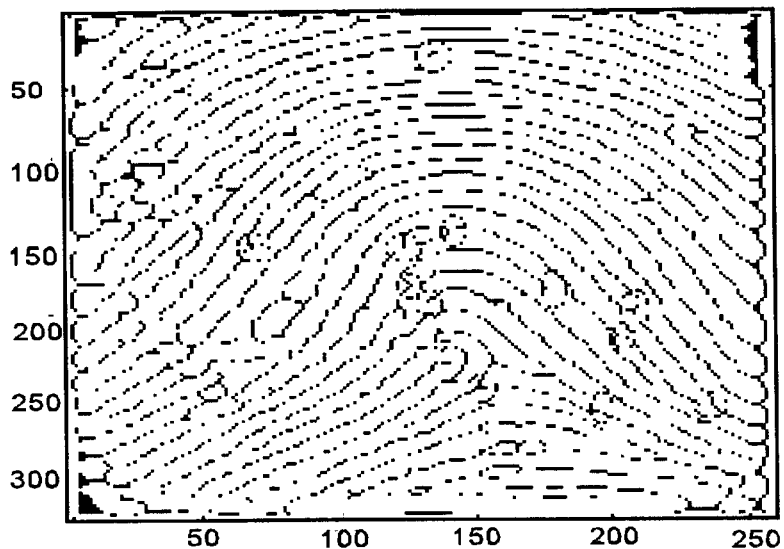
Fig. 37
Fig. 38
Fig. 39

$$A = \begin{bmatrix} 5 & 4 & 3 & 2 & 1 & 0 \\ 4 & 3 & 2 & 1 & 0 & 1 \\ 3 & 2 & 1 & 0 & 1 & 2 \\ 2 & 1 & 0 & 1 & 2 & 3 \\ 1 & 0 & 1 & 2 & 3 & 4 \\ 0 & 1 & 2 & 3 & 4 & 5 \end{bmatrix}$$
Fig. 45
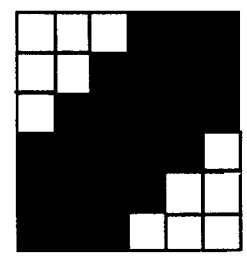
Fig. 46
$$\begin{bmatrix} 7 & 0 & 0 & 8 & 0 & 0 & 1 & 0 & 0 & 2 & 0 & 0 & 3 \\ 0 & 0 & 0 & 0 & 0 & 0 & 0 & 0 & 0 & 0 & 0 & 0 & 0 \\ 0 & 0 & 7 & 0 & 8 & 0 & 1 & 0 & 2 & 0 & 3 & 0 & 0 \\ 6 & 0 & 0 & 0 & 0 & 0 & 0 & 0 & 0 & 0 & 0 & 0 & 4 \\ 0 & 0 & 6 & 0 & 7 & 8 & 1 & 2 & 3 & 0 & 4 & 0 & 0 \\ 0 & 0 & 0 & 0 & 6 & 0 & 0 & 0 & 4 & 0 & 0 & 0 & 0 \\ 5 & 0 & 5 & 0 & 5 & 0 & C & 0 & 5 & 0 & 5 & 0 & 5 \\ 0 & 0 & 0 & 0 & 4 & 0 & 0 & 0 & 6 & 0 & 0 & 0 & 0 \\ 0 & 0 & 4 & 0 & 3 & 2 & 1 & 8 & 7 & 0 & 6 & 0 & 0 \\ 4 & 0 & 0 & 0 & 0 & 0 & 0 & 0 & 0 & 0 & 0 & 0 & 6 \\ 0 & 0 & 3 & 0 & 2 & 0 & 1 & 0 & 8 & 0 & 7 & 0 & 0 \\ 0 & 0 & 0 & 0 & 0 & 0 & 0 & 0 & 0 & 0 & 0 & 0 & 0 \\ 3 & 0 & 0 & 2 & 0 & 0 & 1 & 0 & 0 & 8 & 0 & 0 & 7 \end{bmatrix}$$
Fig. 47
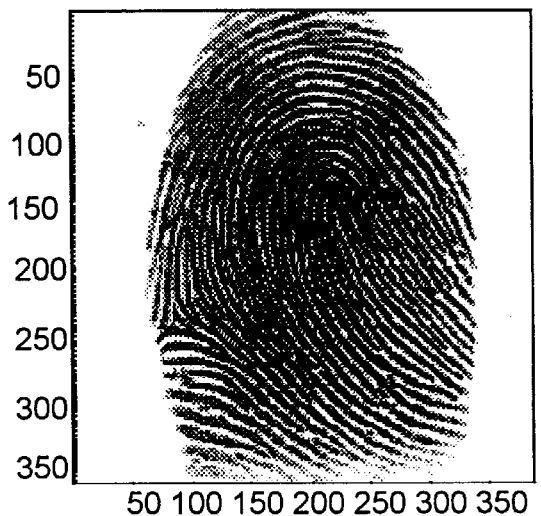
Fig. 48

FINGERPRINT IDENTIFICATION/ VERIFICATION SYSTEM

This application claims the benefit of U.S. Provisional Application No. 60/080,430 filed Apr. 2, 1998. The Provisional Application is incorporated by reference and is attached hereto as Appendix A.

BACKGROUND OF THE INVENTION

This invention relates generally to the field of fingerprint identification/verification systems. More particularly, this invention relates to a fingerprint identification/verification system using two dimensional bitmaps instead of traditional feature extraction.

Two types of matching applications are used for fingerprints. One-to-one verification is used to compare a fingerprint with either a particular template stored on, for example, a smart card, or a template recovered from a database by having the person provide his or her name, Personal Identification Number (PIN) code, or the like. One-to-many identification is used to compare a fingerprint to a database of templates, and is required when a person presents only his or her finger which is then compared to a number of stored images.

Traditional fingerprint identification by feature extraction has been used by institutions like the Federal Bureau of Investigation (FBI) for identifying criminals and is the most common fingerprint identification system. In feature extraction, the pattern of a fingerprint is checked for any special 'features' such as ridge bifurcations (splits) and ridge endings amongst the meandering ridges of the fingerprint. Once each such feature is identified, the location, that is, the distance and direction between the features, and perhaps the orientation of each feature, is determined. By storing only the feature location information, a smaller amount of data can be stored compared to storing the complete fingerprint pattern. However, by extracting and storing only the location of each feature, that is, the one-dimensional point on the fingerprint where the feature is located and, perhaps, the type of feature, information for security purposes is lost because all of the non-feature information is then unavailable for comparisons (matching).

Also, in order to determine the absolute location of the features, an unambiguous starting point (reference point) is selected for the fingerprint. Traditional methods locate a 'core point' as the reference point. This core point is usually selected according to different criteria depending on the type of fingerprint, for example, whorl, circular or other type. Thus, a fingerprint in such a traditional system must first be classified as a known type before the core point can be determined and the features located.

Another difficulty encountered with automated fingerprint identification or verification systems is the inability of the system to differentiate between a real fingerprint, that is, a fingerprint on a finger, and an image or plastic model of a fingerprint. In traditional systems the type of sensor can help, for example, a heat sensor to detect body heat, but these sensors can be defeated.

In addition, identification presents difficulties when the database of possible fingerprints becomes quite large. In traditional fingerprint systems, each type of fingerprint is categorized and the types of features provide additional subclasses. Nevertheless, the number of classes and subclasses is quite small when compared to the number of fingerprints which may be in any particular class or subclass. Also, once a class or subclass is selected, possible matches in a different class or subclass of the same level of the hierarchy are not checked. Thus, for fingerprints which do not clearly fall within a particular class or subclass, there may be stored fingerprints in the database which are not checked. Accordingly, a search for a matching fingerprint image on file can be both time consuming and result in a false indication that the particular fingerprint is not on file.

OBJECTS AND SUMMARY OF THE INVENTION

An object of the present invention is to provide a fingerprint identification system which identifies fingerprints more accurately than prior systems.

Another object of the present invention is to identify fingerprints by comparing entire two dimensional regions of fingerprint images rather than just the locations of features.

An additional object of the present invention is to accurately and efficiently find a reference point in the image from where to start the identification or verification process.

A further object of the present invention is to determine dynamics of the fingerprint as the image is being made to differentiate a true fingerprint from a false/fake fingerprint placed on the sensor.

Another object of the present invention is to establish a non-hierarchical database which allows for rapid matching of a candidate fingerprint and matching without requiring that the candidate fingerprint belong to a particular class.

A further object of the invention is to provide a fingerprint processing method, and a device for accomplishing the method, having the steps of: (1) obtaining an image of a fingerprint comprising ridges and valleys; (2) searching the image to locate a reference point; and (3) selecting the reference point and a region in the vicinity of the reference point as a recognition template for the image. This method can have the following additional steps: (1) applying the fingerprint to a scanning device; (2) scanning the fingerprint to generate an image signal; and (3) storing the image signal as a digital image. In addition, this method can include any or all of the following sub-methods:

(A)—(1) vectorizing the digital image; (2) selecting a starting sub-area in the vectorized image; (3) scanning from the starting sub-area along an orientation of each subsequent sub-area to locate a first sub-area having a horizontal orientation, the first sub-area included in a first horizontal structure; (4) scanning from the first sub-area across acceptable structures and along a path of acceptable sub-areas until an unacceptable sub-area is located; and (5) selecting the center point of the last scanned acceptable sub-area as the reference point;

(B)—(1) calculating the geographic center of the digital image; and (2) selecting the geographic center as the reference point; or (C)—(1) binarizing the digital image; (2) determining the row of the digital image which has the greatest number of binary transitions; (3) determining the column of the digital image which has the greatest number of binary transitions; and (4) selecting a point in the image by following a path starting from a point in the image having the row and the column as coordinates.

Also, the searching step of this method can include the following steps: (1) selecting a starting point; (2) following along at least one ridge proximate the starting to locate a ridge of a first type; (3) selecting adjacent ridges of the first type along a predetermined path to locate a ridge of a second type; and (4) selecting a point on the last located ridge of the first type as the reference point.

In addition, the selecting step of this method can include the following steps: (1) selecting the region to include the reference point, the region having a size and a shape; (2) storing the recognition template; (3) selecting the region to include the reference point; (4) selecting other regions, each of the other regions having a respective size and a respective shape, each such other region located with respect to the reference point according to relative location information; and (5) selecting the other regions and the respective relative location information for each respective other region as part of the recognition template for the image.

In addition, this method can include the following steps: (1) storing the recognition template; (2) encrypting one or more of the region, the other regions, and the relative location information; and (3) compressing one or more of the region, the other regions, and the relative location information.

An additional object of this invention is to provide a fingerprint matching method, and a device for accomplishing the method, having the steps of: (1) obtaining an image of a fingerprint comprising ridges and valleys; (2) searching the image to locate a reference point; (3) selecting the reference point and a region in the vicinity of the reference point; (4) selecting at least one recognition template, each recognition template comprising a template reference point and a template region; (5) correlating at least a portion of the region with the template region to generate a correlation result; and (6) determining whether the correlation result exceeds a predetermined matching requirement. This method can also include the following steps: (1) obtaining from the recognition template, relative location information of at least one other template region; (2) selecting another region from the image utilizing the relative location information with respect to the template reference point; (3) correlating at least a portion of the another region with the other template region to generate a correlation result; and (4) determining whether the correlation result exceeds a predetermined matching requirement.

Another object of this invention is to provide a fingerprint processing method, and a device for accomplishing the method, having the following steps: (1) obtaining sequential multiple images of a fingerprint comprising ridges and valleys; (2) determining dynamics of the obtaining step procedure by comparing the multiple images to each other. The method can also have the following additional step: determining from the dynamics if the fingerprint is real.

A further object of this invention is to provide a fingerprint information storage method, and a device for accomplishing the method, having the following steps: (1) obtaining from a fingerprint values for each of a number of fingerprint characteristics; (2) assigning each of the values to a respective coordinate, the coordinates defining a point in a dimensional space having the number of dimensions; and (3) associating information concerning the fingerprint with the point. This method can also include the step of locating information concerning other fingerprints based on the proximity of other points in the dimensional space associated with other respective fingerprints.

Also, an object of the present invention is to provide a fingerprint processing device, and a method for operating the device, having: (1) a sensor for detecting a fingerprint and for generating an image signal corresponding to the fingerprint; (2) a processor for receiving the image signal and for identifying a reference point and a region in the vicinity of the reference point in an image formed from the image signal; and (3) a storage device for storing information concerning the reference point and a portion of the image. This device may also include a correlator for comparing information received from the storage device and information concerning the region in the vicinity of the reference point.

An additional object of the present invention is to provide a storage template, and a method for creating the template, for a fingerprint processing system having: (1) a first region bitmap; (2) a reference point location; (3) outlying region bitmaps; and (4) relative location information, the relative location information corresponding to the location of each of the outlying region bitmaps with respect to the reference point location.

These objects and other objects, advantages, and features of the present invention will become apparent to those skilled in the art upon consideration of the following description of the present invention.

DETAILED DESCRIPTION OF THE INVENTION

Figure 1:
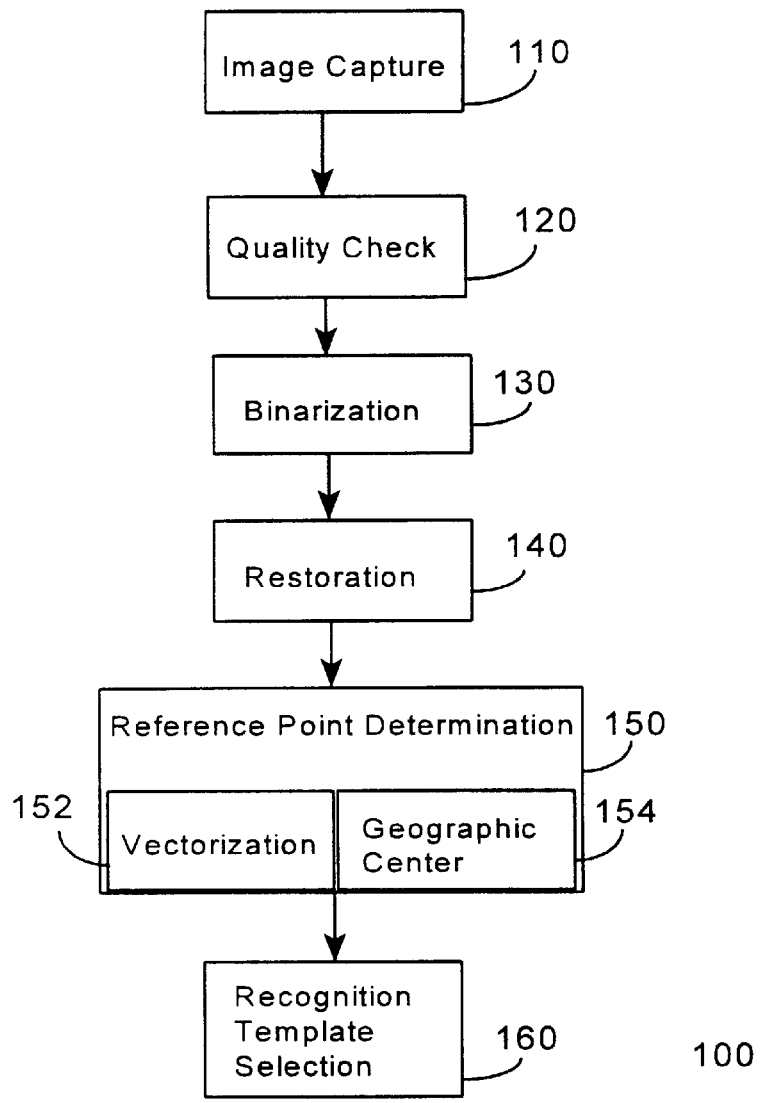
FIG. 1 is a flow diagram illustrating an enrollment process according to an embodiment of the present invention.

While this invention is susceptible of embodiment in many different forms, the drawings show and the specification herein describes specific embodiments in detail. However, the present disclosure is to be considered as an example of the principles of the invention and is not intended to limit the invention to the specific embodiments shown and described. In the description below, like reference numerals are used to describe the same, similar or corresponding parts in the several views of the drawing.

The present invention is described below in two main sections: (1) an enrollment procedure and device; and (2) a matching procedure and device. The matching procedure and device section also describes the use of finger dynamics and a non-hierarchical database as employed in the present invention.

Figure 2:
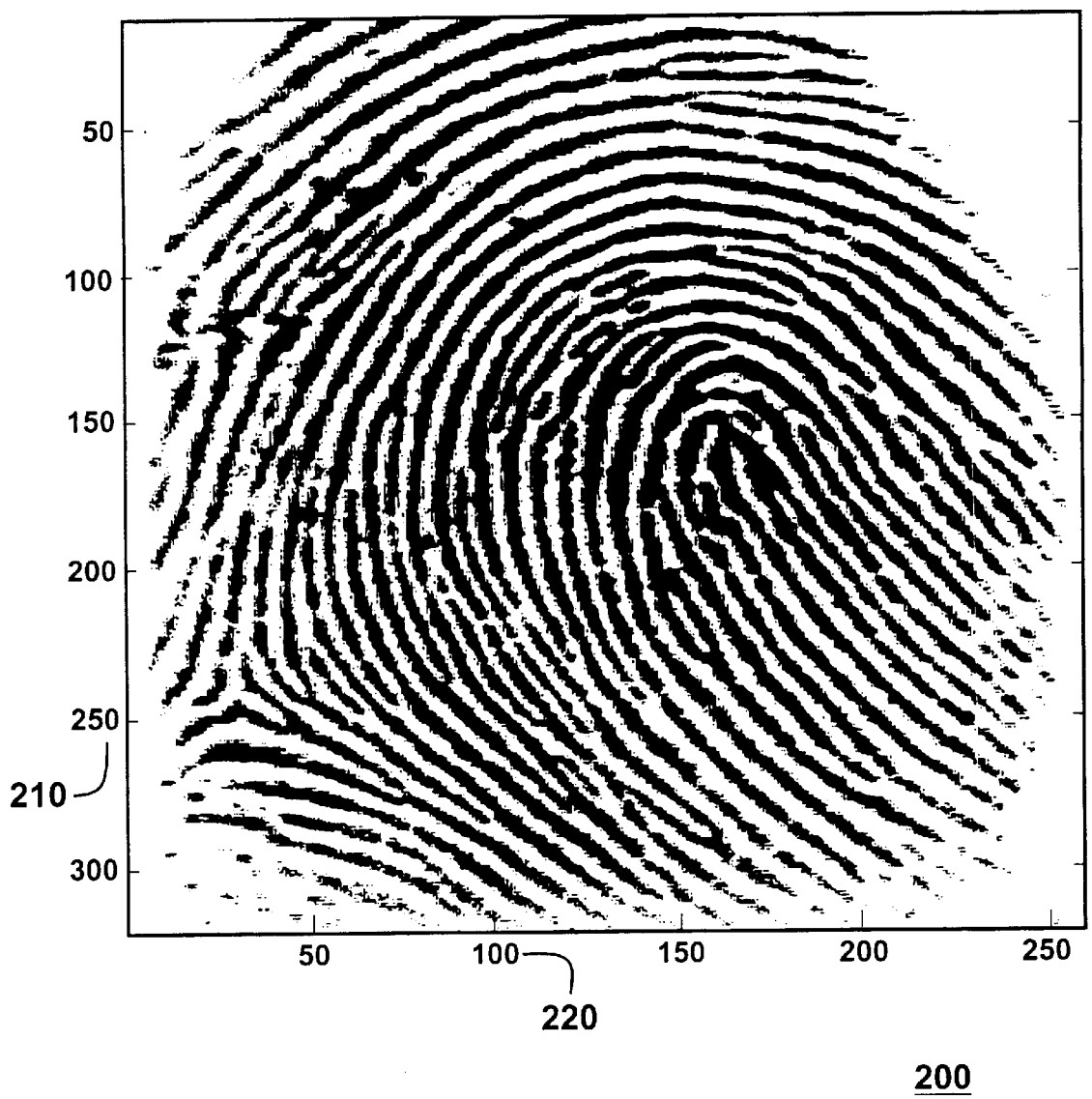
FIG. 2 is a binarized version of a captured image according to one embodiment of the present invention.

FIG. 1 illustrates a procedure for selecting information to be stored as a template by enrollment 100, for example to register authorized people, according to one embodiment of the present invention. In this embodiment, the captured image is a digital image. A binarized version of the captured image is illustrated in FIG. 2. This binarized image is organized into an orthogonal grid 200 having rows 210 and columns 220 of picture elements or pixels. Each pixel is encoded to a gray-scale value. The rows 210, the horizontal orientation, are numbered in increasing order moving down from the part of the image corresponding to the part of the fingerprint closest to the fingertip; and the columns 220, the vertical orientation, are numbered in increasing order from left to right. Also, the terms 'up', 'down', 'left', 'right', and variations thereof, are used in this specification to refer to the top (lower row numbers), bottom (higher row numbers), leftside (lower column numbers), and rightside (higher column numbers), in an image, respectively. However, the present invention can be implemented using other types of images and image organizations, such as for example, a hexagonal grid or an analog image.

The enrollment procedure 100 according to one embodiment of the present invention is described below with respect to each step of the procedure.

Image Capture 110: The first step in enrollment 100 is to capture the image with an image capturing device or sensor. The sensor can be, for example, a heat sensor, a light sensor, an optical sensor, a silicon sensor, or any other technology used to capture a fingerprint image. The sensor is coupled to a signal processor and/or microprocessor with sufficient read only memory (ROM) and random access memory (RAM) for operating on the image signal produced by the sensor.

If high security is required, such as for access to high-security computer network, the enrollment process 100 could be monitored while the person's fingerprint is placed on the sensor to ensure a high quality image is captured for storage as a template. Lower security, such as for access to an automatic teller machine (ATM) lobby, however, does not require as much, if any, supervision during enrollment 100 since a lower quality template can be tolerated.

Quality Check 120: The fingerprint image is checked for dryness or wetness. If the image is 'too dry' the pressure applied to the sensor was too light or the sensor failed to detect parts of ridges because of fingertip dryness. If the image is 'too wet', moisture on the finger 'flooded' the fingerprint valleys. Wetness or dryness is detected by analyzing the image for too few dark pixels (dryness) or, too many dark pixels and continuous dark areas (wetness). If the image is rejected, the person is asked to correct the problem and another image is taken.

Binarization 130: Once an image of the appropriate quality is captured 110, 120 the gray-level image is converted into a black-and-white (binarized) image, see FIG. 2, of the sensed fingerprint. This binarization is extremely sensitive to the quality of the image. Binarization 130 is performed using a gray-scale threshold. Thus, for example, a pixel having a gray-scale value above a threshold value is determined to be black, and a pixel having a gray-scale value level below the threshold value is determined to be white. The threshold value can be global (the same threshold value is used for the entire image), or local (different threshold values are calculated separately for different areas of the image).

Also, in one embodiment of the present invention, to aid in binarization 130, information from the ridge/valley directions are used to enhance the binarized image. For example, an isolated pixel which has a gray-scale value just high enough to be considered black and thus, part of a ridge, will instead be set to white if all the surrounding pixels are considered to be in a valley. This enhancement is particularly useful for lower quality or noise-affected images. Another embodiment of the present invention combines both local thresholds and ridge/valley direction information from the same area as part of binarization 130.

Restoration 140: Restoration is similar to, and is interconnected with, binarization 130. However, restoration 140 is performed after binarization 130. Basically, restoration 140 takes advantage of knowledge of how fingerprints are known to appear, for example, the generally continuous nature of fingerprint ridges. Techniques such as the use of local ridge/valley directions described above are also used for restoration 140. Another restoration technique determines a pixel's value based on the particular combination of the neighboring pixel values. Other restoration methods consider and restore the image based on expected ridge/valley widths and other physical fingerprint characteristics.

Reference Point Determination 150: After the image is binarized 130 and restored 140, a reference point for the image must be selected. Finding a repeatedly locatable reference point has traditionally been extremely complex because of the many different types of fingerprints. Even in traditional manual fingerprint classification, which has a large set of rules for identifying the reference points for many types of fingerprints, reference points cannot be defined for some types of fingerprints.

However, in one embodiment of the present invention only two procedures are required. The first procedure 152 is based on a vectorization of the gray-scale image. The second procedure 154, which is used only if the first procedure 152 is unable to locate a reference point, locates the geographic center of the image. Alternatively, the second procedure 154 can be based on counting the ridges in a binarized image, or by calculating fast Fourier transforms (FFTs) of the fingerprint image and selecting the point corresponding to the dominant frequencies.

Figure 4:
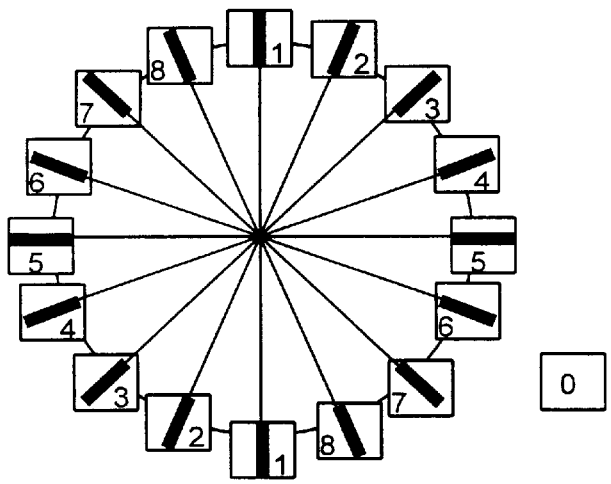
FIG. 4 illustrates the possible sub-area orientations according to an embodiment of the present invention having eight possible orientations.
Figure 3:
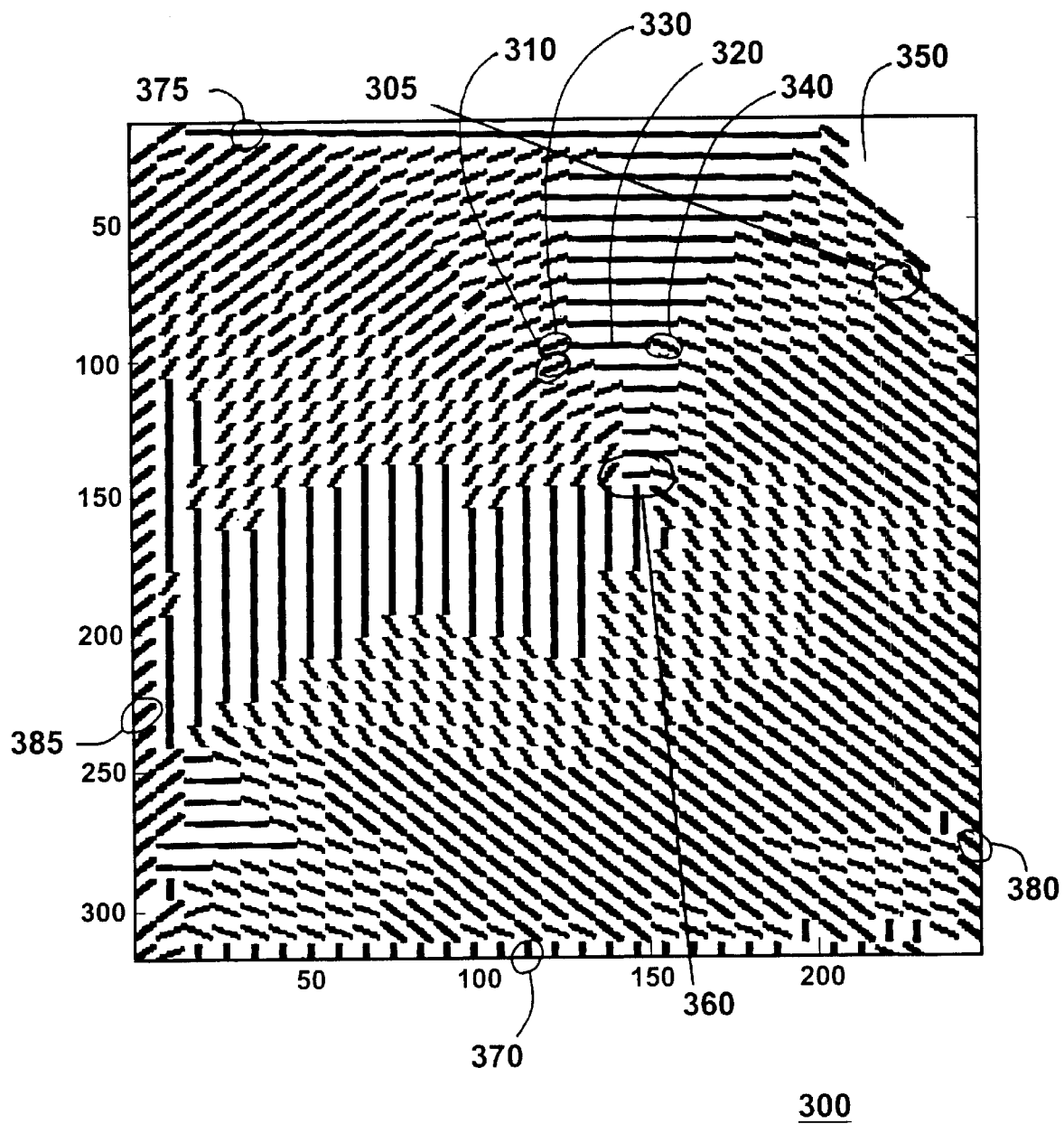
FIG. 3 is a vectorized version of the same captured image which is binarized in FIG. 2 according to one embodiment of the present invention.

The first procedure 152 locates a reference point from a vector representation of the gray-scale image, that is, a vectorized image 300. FIG. 3 illustrates such a vectorized image. Vectorization 152 is performed by dividing the image into sub-areas and by assigning an orientation to each sub-area 305. FIG. 4 illustrates the possible sub-area orientations according to the embodiment of the present invention shown in FIG. 3. With this first procedure 152, the reference point is defined as either the center pixel of the last of the leftmost of two sub-areas of the image defining a 'roof' structure, or the center pixel of the last middle (or, if there are two middle sub-areas, the left middle) sub-area 360 of a horizontal line structure which is encountered when searching downward from the top of the vectorized image 300.

Figure 7:
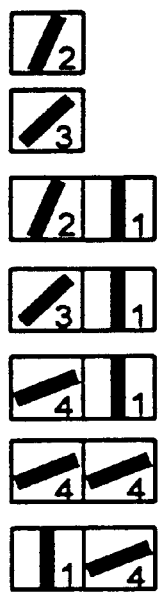
FIG. 7 illustrates the possible acceptable left endpoints for an acceptable horizontal line structure according to one embodiment of the present invention.
Figure 8:
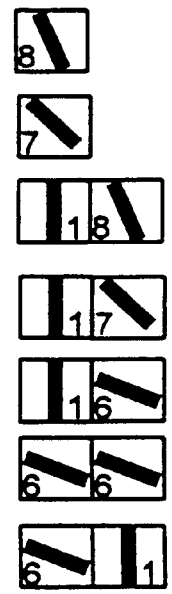
FIG. 8 illustrates the possible acceptable right endpoints for an acceptable horizontal line structure according to one embodiment of the present invention.
Figure 5:
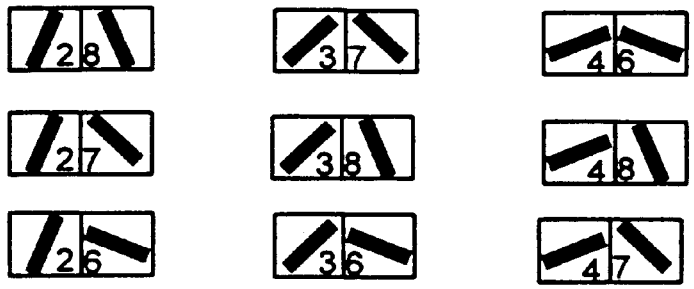
FIG. 5 illustrates the acceptable roof structures according to one embodiment of the present invention.
Figure 6:
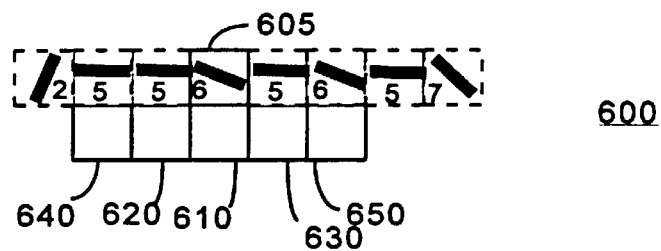
FIG. 6 illustrates the candidate sub-areas during a downward search according to one embodiment of the present invention.

FIG. 5 illustrates the acceptable roof structures. Basically, a roof structure is defined as two sub-areas pointing upwards and askew towards each other, that is, 2, 3 or 4 as a left sub-area and 6, 7 or 8 as a right sub-area. FIG. 6 illustrates an acceptable horizontal line structure according to one embodiment of the present invention. Also, FIGS. 7 and 8 illustrate acceptable left and right endpoints, respectively, for an acceptable horizontal line structure according to one embodiment of the present invention. The acceptable left endpoint patterns shown in FIG. 7 have orientation numbers are 2; 3; 1 followed to the left by a 2, 3 or 4; 4 followed to the right by a 4; or 4 followed to the left by a 1. The acceptable right endpoint patterns shown in FIG. 8 have orientation numbers are 7; 8; 1 followed to the right by a 6, 7 or 8; 6 followed to the left by a 6; or 6 followed to the right by a 1.

Most fingerprints have roof structure ridges below multiple horizontal ridges which gradually increase in curvature towards the center of the fingerprint until a ridge is so curved as not to be considered either a roof structure or a horizontal line structure. In other words, the reference point located with this first procedure 152 is the topmost point of the innermost upward curving ridge, that is, where the ridge almost curves, or does curve, back on itself.

To locate the reference point in the vectorized image 300, the first procedure 152 begins by searching for a first horizontal line structure with endpoints having orientations pointing upwards and inwards. Then, the procedure 152 searches downward until acceptable horizontal line structures and roof structures give way to other types of, though usually almost vertical, structures. Should this transition from horizontal line structures and roof structures not be found, the reference point sub-area 360 is presumed to have been missed. The first procedure 152 indicates that the downward search has passed the reference point when the acceptable horizontal line structures begin to lengthen again, that is, become much longer. While searching upwards, the scan searches for a roof structure as in the downward search, but continues the search until the next horizontal line structure is encountered before selecting the reference point.

The reference point located according to the first procedure 152 is stable over any number of images of the same fingerprint while also being located in an area with a high degree of information content, that is, an area with little redundant information such as parallel ridges. This location in a high information area aids in the matching procedure. Furthermore, this procedure locates the same reference point even if the fingerprint is presented at different angles with respect to the sensor. For example, the same reference point will be located even if one image of the fingerprint is rotated +/−20 degrees with respect to another image of the same fingerprint.

Locating the reference point is repeated for a multiple number of images of the same fingerprint to verify that the reference point is stable over these images and to ensure that when the fingerprint is later imaged for identification/verification, the same reference point is located. In one embodiment, ten images were found sufficient.

While the present invention can operate with a vectorization using N orientations, with a minimum of N=2, the embodiment illustrated in FIG. 3, has eight possible orientations that is, N=8. In the embodiment shown in FIG. 3, each vector represents the predominant orientation of an 8 pixel by 8 pixel sub-area of the image. The size of the sub-area used for selecting an orientation generally corresponds to the resolution of the image. For example, an 8 pixel by 8 pixel sub-area is sufficient for a digital image of 500 dots per inch resolution. In FIG. 3, the eight orientations are evenly spaced but the direction of the orientations is not distinguished. For example, the vectors of 90 degrees and 270 degrees have the same orientation.

As illustrated in FIG. 4, each of the orientations can be assigned a number:

| Vector (degrees) | Orientation Number |
| --- | --- |
| 90 and 270 (vertical) | 1 |
| 67.5 and 247.5 | 2 |
| 45 and 225 (left oblique) | 3 |
| 22.5 and 202.5 | 4 |
| 0 and 180 (horizontal) | 5 |
| 157.5 and 337.5 | 6 |
| 135 and 315 (right oblique) | 7 |
| 112.5 and 292.5 | 8 |
| non-defined, background | 0 |

Most conventional vectorization methods produce a good representation of the original image once the thresholds for the foreground and background of the image are determined. To define this boundary, in one embodiment of this invention and as illustrated in FIG. 3, boundaries of the vector image foreground are set according to the following rules, applied in order:

1. The orientation at the bottom of every column is vertical 370;

2. The orientation at the top of every column is horizontal 375;

3. The rightmost orientation of every row is right oblique 380; and

4. The leftmost orientation of every row is left oblique 385.

These boundary conditions allow the search for a reference point to start virtually anywhere in the vectorized image and iteratively follow a set procedure to locate the same reference point.

The downward search according to one embodiment of the present invention is described in further detail below, as Steps A, B, C and D and with reference to FIGS. 3–11.

Step A. (Start): Start at any sub-area in the foreground of the vectorized image. In one embodiment, the starting point 310 is the intersection of the vertical column of the geographic center of the image, and the horizontal row of one-third of the way to the top of the image from the geographic center.

Figure 9:
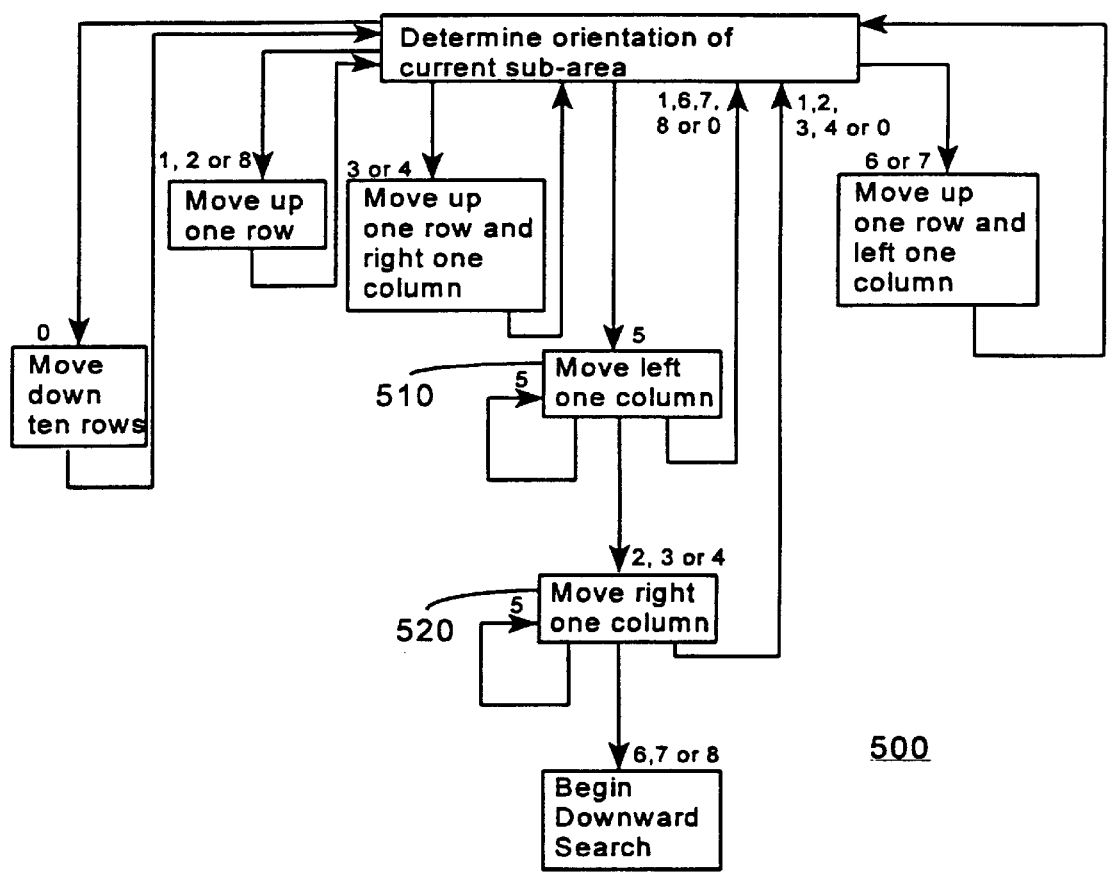
FIG. 9 is a flow diagram illustrating a first horizontal line structure search according to one embodiment of the present invention.

Step B. (Search for first horizontal line structure): Search by following the orientation of each sub-area in the image generally upwards from sub-area to sub-area until a first horizontal line structure 320 is encountered. A first horizontal line structure 320 has a left endpoint 330 with an orientation number of 2, 3 or 4 and a right endpoint 340 with an orientation number of 6, 7 or 8. This first horizontal line structure search 500 is illustrated in FIG. 9 and is performed as follows:

| Current Sub-area | Next Sub-area |
| --- | --- |
| 1, 2 or 8 | move up one row |
| 3 or 4 | move up one row, move right one column |

-continued

| Current Sub-area | Next Sub-area |
| --- | --- |
| 5 | perform a left endpoint search for a first horizontal line structure |
| 6 or 7 | move up one row, move left one column |
| 0 | move down ten rows |

Orientation number 0 means the current sub-area is in the background 350 of the image which means that the search has moved too far up in the image. Therefore, the search moves ten rows downward before continuing. When a sub-area with a horizontal orientation, that is orientation number 5, is encountered, a search is made to determine if the first horizontal line structure has been found. If no first horizontal line structure is found after, for example, 100 iterations of Step B, this first procedure 152 has failed to locate a reference point, and the second procedure 154 is used.

The left endpoint search 510 for a first horizontal line structure is performed as follows:

| Current Sub-area | Next Sub-area |
| --- | --- |
| 1, 6, 7, 8 or 0 | move left one column, return to first horizontal line structure search |
| 2, 3 or 4 | move right one column, perform right endpoint search for first horizontal line structure |
| 5 | move left one column |

The right endpoint search 520 for a first horizontal line structure is performed as follows:

| Current Sub-area | Next Sub-area |
| --- | --- |
| 1, 2, 3, 4 or 0 | move right one column, return to first horizontal line structure search |
| 5 | move right one column |
| 6, 7, 8 | begin downward search |

Figure 10:
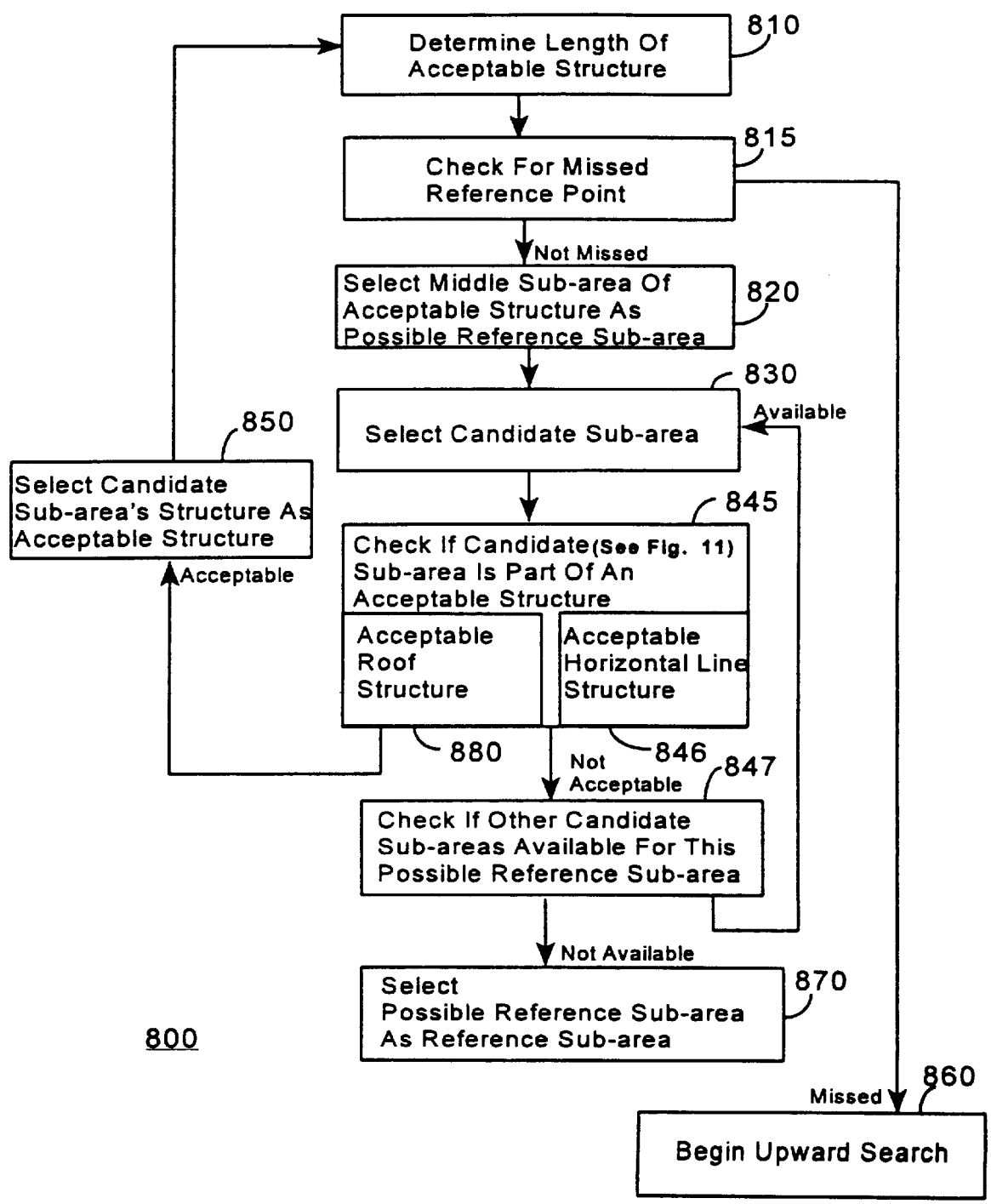
FIG. 10 is a flow diagram illustrating a downward search for the reference point according to one embodiment of the present invention.

Step C. (Downward Search): Searches downwards from the first horizontal line structure 320 until the reference point is found, or the search has skipped the reference point. A skipped reference point is indicated by the length of the acceptable horizontal line structures because above the reference point the acceptable horizontal line structures get smaller in the downward direction, but below the reference point the acceptable horizontal line structures get longer in the downward direction. This downward search procedure is illustrated in FIG. 10. Roof structures, as illustrated in FIG. 5, can be considered the shortest acceptable horizontal line structures and are acceptable structures. Also, while the first horizontal line structure 320 is a type of acceptable horizontal line structure, acceptable horizontal line structures encompass a greater degree of variation, see FIGS. 6 and 11.

Figure 11:
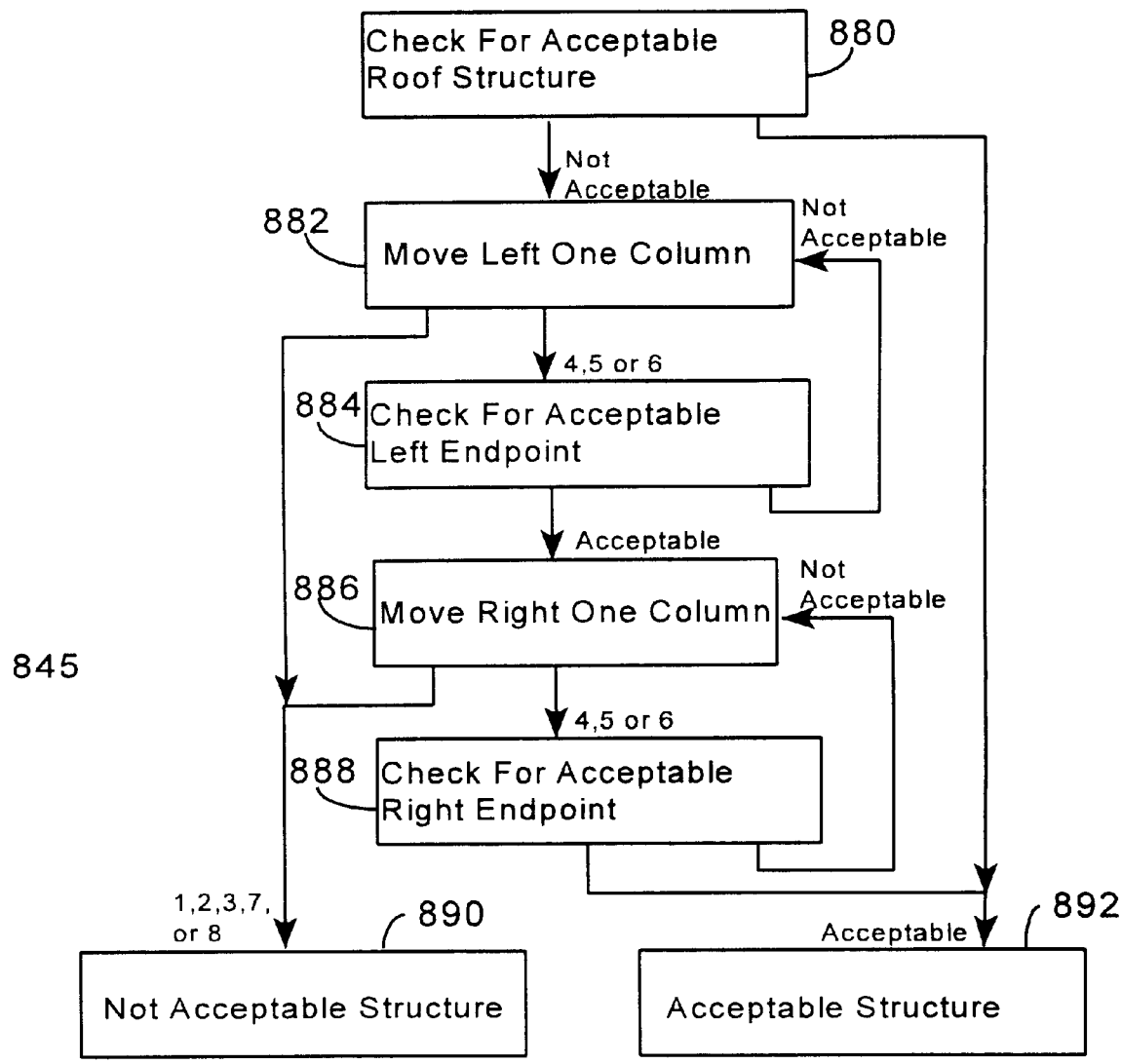
FIG. 11 is a flow diagram illustrating the scan of a structure to determine if the structure is acceptable according to one embodiment of the present invention.

The first step in the downward search is to determine the length 810 of the current acceptable structure 600 by counting the number of sub-areas of the acceptable structure. Then, as illustrated in FIGS. 6, 10 and 11, select 820 the middle sub-area 605 of the acceptable structure as the possible reference sub-area and investigate 830 the following candidate sub-areas, in the following order: (1) down one row 610; (2) down one row, left one column 620; (3) down one row, right one column 630; (4) down one row, left two columns 640; (5) down one row, right two columns 650.

If any of these candidate sub-areas are part of an acceptable structure 845,847 select this acceptable structure 850 for determining the next middle sub-area for the next iteration of step C. However, if the length of the acceptable structure 600 is much longer, for example six times longer, than the shortest length of the acceptable structures encountered so far 815, the reference point is considered to have been skipped and an upward search needs to be performed 860, see Step D.

If no acceptable structure, that is, a horizontal line or a roof structure, has been located among the candidate sub-areas 847, the possible reference sub-area is, in fact, the actual reference sub-area 360, and the center pixel of the actual reference sub-area is the reference point.

The acceptable horizontal line structure search 846 is performed as follows:

| Current Sub-area | Next Sub-area |
| --- | --- |
| 1, 2, 3, 7, or 8 | select next candidate sub-area |
| 4, 5 or 6 | perform acceptable left endpoint search |

The acceptable left endpoint search 882, 884 is performed as follows:

| Current Sub-area | Next Sub-area |
| --- | --- |
| 4, 5 or 6 | move left one column, check for acceptable left endpoint |
| 1, 2, 3, 7, or 8 | select next candidate sub-area |

If an acceptable left endpoint is found, the acceptable right endpoint search 886, 888 is performed as follows:

| Current Sub-area | Next Sub-area |
| --- | --- |
| 4, 5 or 6 | move right one column, check for acceptable right endpoint |
| 1, 2, 3, 7, or 8 | select next candidate sub-area |

If both an acceptable right endpoint and an acceptable left endpoint are found 892, the horizontal line structure is acceptable and the middle sub-area of this acceptable horizontal line structure is used to determine the next candidate sub-areas.

Step D. (Upward Search) Searches upwards according to similar rules as Step C, except the search for acceptable structures is performed in the upward directions.

Thus, according to one embodiment of the present invention, a stable reference point can be identified by locating the first point in the fingerprint image, scanning downward, which has a greater curvature than even the roof structures, for example, a left sub-area orientation of 1 and a right sub-area orientation of 8. Since the structures above this point are common to virtually all kinds of fingerprints, that is, primarily parallel meandering ridges, finding a starting point and then searching downwards will almost always locate a stable reference point.

The second procedure 154, according to one embodiment of the present invention, is used to locate the geographic center only when the first procedure 152 fails to locate the reference point.

The geographic center of the binarized fingerprint image 200 is defined as the pixel in the foreground of the image where the same number of pixels are located above the point as below and the same number of pixels are located to the right as to the left. Thus, the foreground of the image must be separately identified from the background.

In one embodiment of the present invention, the boundary of the foreground is determined using the variance of the pixel values. The pixel values only vary slightly over the entire background, whereas in the foreground the pixel values vary significantly because the ridge structures have significant variation between the valleys which, in one embodiment of the present invention, are white and the ridges which, in one embodiment of the present invention, are black. Thus, by calculating the variance of the pixels, the boundary between the foreground and background can be determined.

An alternative procedure for locating the foreground boundary of the image is to find the first pixel of every row and column that corresponds to a part of a ridge when searching toward the center of the binarized image 200 from each edge of the image. In one embodiment of the present invention such a pixel has a value higher than a certain threshold whereas the background has pixels having values below the certain threshold. Because the ridges are in the foreground, the pixels so located define the boundary of the foreground.

Once the foreground boundary has been determined, the number of foreground pixels in each row and column are counted and the column that has as many foreground pixels to the left as to the right and the row that has as many foreground pixels above as below are selected as the coordinates of the reference point for the image.

An alternative first or second procedure 152, 154 for finding a reference point is based on ridge counting using the binarized, restored image. In this alternative procedure, the number of ridges crossing each vertical and horizontal grid line in the image are determined. The point where the row and the column having the highest respective ridge counts intersect is selected as a starting point. This row is selected as the reference point row. From this starting point, a search follows along three neighboring ridges to the topmost point (lowest row number) and this column is selected as the reference point column. These two steps, are described in greater detail below as Steps A and B.

A. Along each row and column, the search counts all transitions from black to white and white to black. Then the search selects the point (row, column) with the highest ridge count, that is the greatest number of transitions, as a starting point, or if three or more rows/columns having the same ridge count, the middle row/column is selected.

B. Using the row value from the starting point, the search then selects the reference point column by following the ridge closest to the starting point and the two closest neighboring ridges upwards to the respective top points. The average of these three ridge top points is selected as the reference point column.

Figure 12:
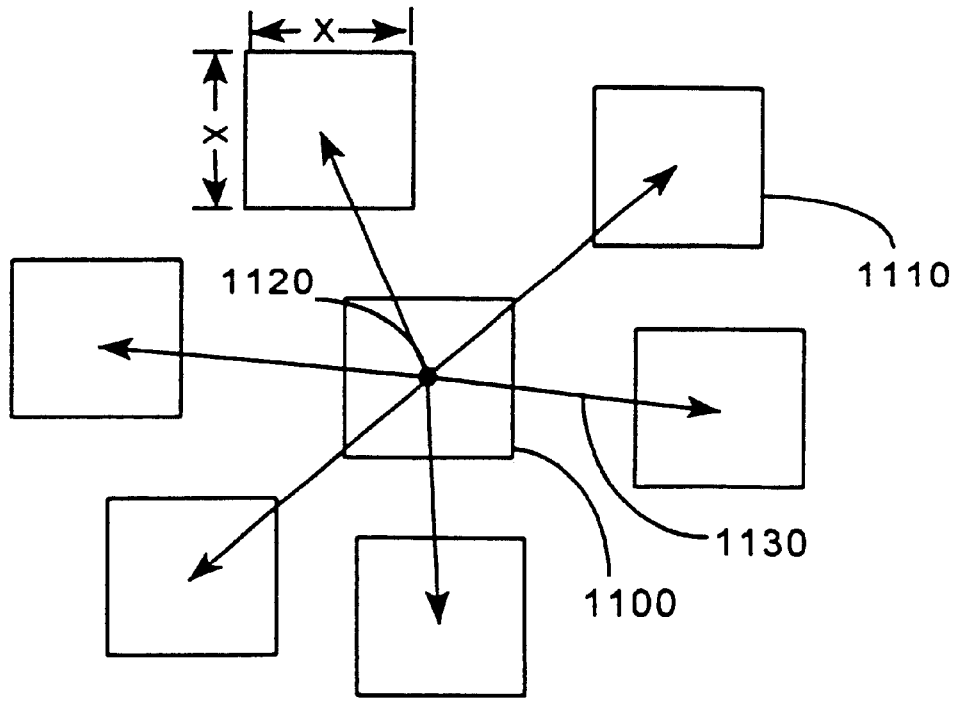
FIG. 12 illustrates the center region, outlying regions, and the location vectors for a recognition template according to one embodiment of the present invention.

Recognition Template Selection 160: After the reference point has been determined, both the reference point and a first region of the binarized image is selected for storage as part of a recognition template. As illustrated in FIG. 12, in one embodiment of this invention, a region centered on the reference point 1120 is selected as a 'center region' 1100. This center region, according to one embodiment of the invention, is a square having a size of 48 pixels by 48 pixels.

Also, additional outlying regions 1110 of the binarized image are selected for storage in the recognition template. In one embodiment of the present invention, four to eight outlying square regions 1110 are selected, each outlying region having a size of 48 pixels by 48 pixels. The outlying regions 1110 can be selected to be neighboring, proximate, or in the vicinity of the center region 1100. However, this invention also encompasses center regions and outlying regions of different sizes, shapes and more distant locations. The size, shape and location of the regions can be selected so as to maximize the useful information in accordance with, for example, the number of pixels available from the sensor, or other considerations. The outlying regions 1110 are located with respect to the reference point 1120 using location information 1130 which is also stored in the recognition template. This location information is illustrated in FIG. 12 by vectors 1130 originating at the reference point.

Outlying regions 1110 can be selected based on fixed positions relative to the center region 1100 or reference point 1120, or in one embodiment, the fingerprint binary image can be scanned for features and each of the feature locations can be used as the basis for defining outlying regions. By selecting outlying regions 1110 including features, more information is stored than when outlying regions containing parallel ridges are selected. More information is conveyed in features because features have less redundant information than parallel ridges and, thus, are more easily distinguished when compared. The features are initially located using conventional methods, for example, following a ridge line to the point where the ridge ends or splits (bifurcates). Once identified, the outlying regions 1110 are selected to include as many feature locations as possible thereby maximizing the amount of useful information being stored. However, if the image lacks a sufficient number of features for the number of outlying regions 1110 required, the remaining outlying regions can be selected using default locations.

Once selected, the reference point 1120, the pixels of the center region 1100, the pixels of the outlying regions 1110, and the location information 1130 are stored in the recognition template. All or part of the recognition template may be compressed and/or encrypted before being stored.

Figure 14:
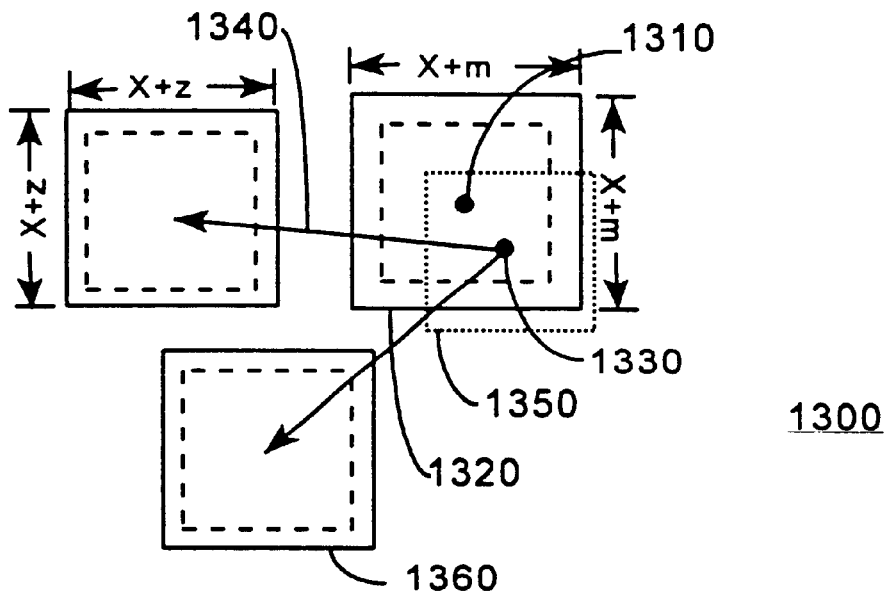
FIG. 14 illustrates the matching procedure for both the center regions and the outlying regions according to one embodiment of the present invention.
Figure 13:
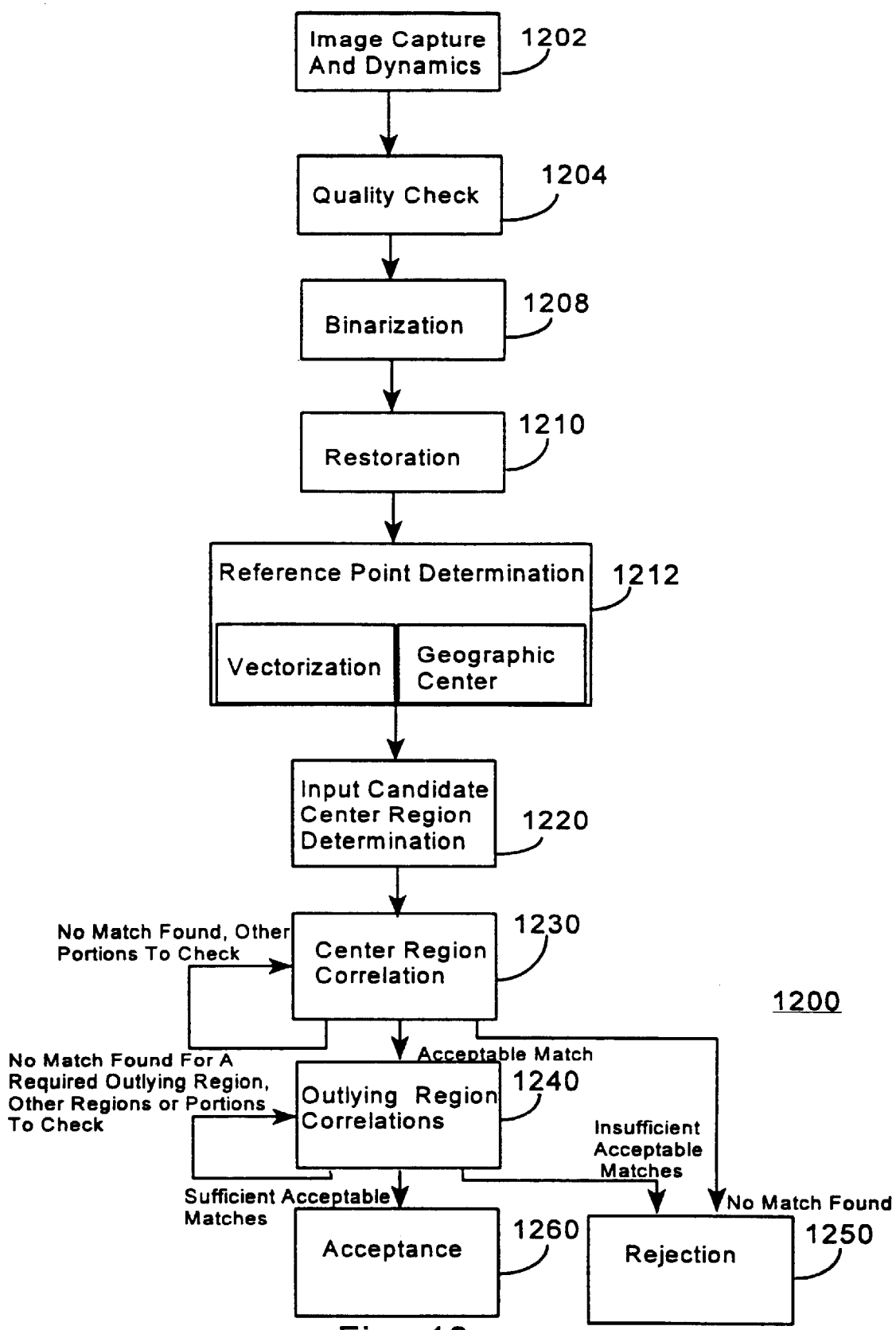
FIG. 13 is a flow diagram illustrating the matching process according to one embodiment of the present invention.

The matching procedure is described below with respect to FIGS. 13 and 14. This matching procedure can be used for both identification and verification. If verification is desired, a particular recognition template, such as for example, a template stored on a smart card, is compared to the candidate image information. If identification is required, a search of a recognition template database is performed based on particular characteristics of the candidate image information to locate potential matching recognition templates. Identification, therefore, requires a series of matching procedures.

Image Capture and Dynamics 1202: When a finger is pressed against the sensor to capture one or more images of the candidate fingerprint, the percentage of black pixels change from approximately zero to around 50% of the pixels. In one embodiment, a threshold is used to determine whether a sufficient number of pixels have become black so that matching can be performed.

In one embodiment of the present invention, multiple images of the candidate fingerprint are acquired at the maximum possible speed allowed by the system which is between 5 and 50 images per second while the finger is pressed against the sensor. Each of these candidate images, if time permits, can be processed separately using the matching procedure 1200. By using multiple images, dynamic properties of the fingerprint capture procedure can be sensed. For example, the multiple images can be compared to each other to improve image quality and to verify the stability of the reference point.

One advantage of acquiring images at a rate of at least 5 to 50 times per second (Hertz) is that fake fingerprints can be detected. This detection is possible because the images captured from a real finger are not instantly stable. Fake fingerprints, such as formed from silicone or rubber, or a paper copy of a fingerprint do not exhibit this kind of instability.

Figure 15:
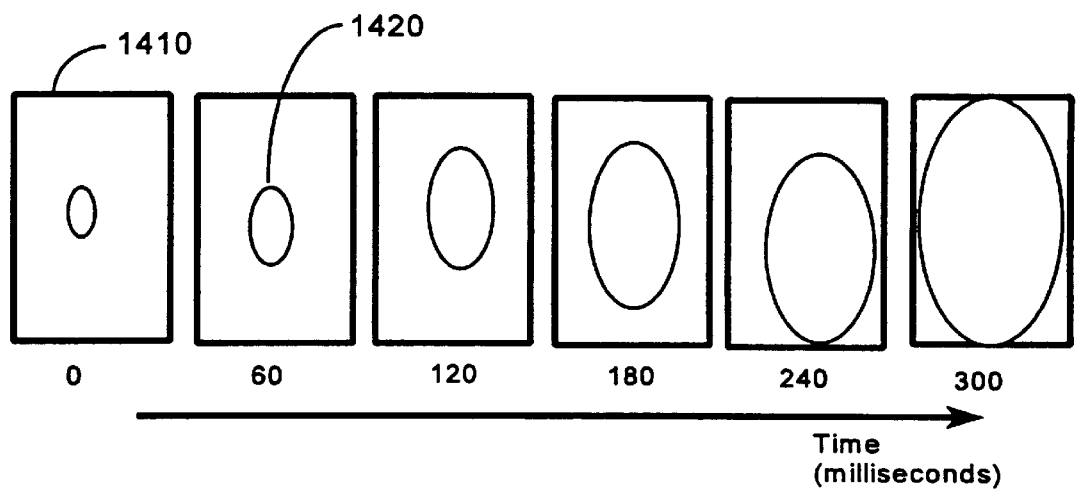
FIG. 15 illustrates the increasing coverage as a fingerprint is dynamically sensed to form an image according to one embodiment of the present invention.
Figure 16:
Figure 17:
Figure 18:
Figure 19:
Figure 20:
Figure 21:
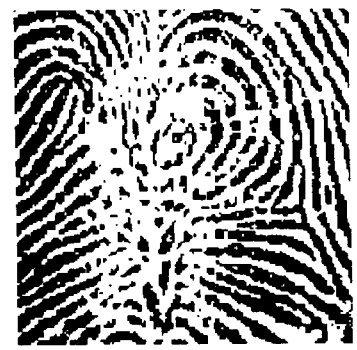
Figure 22:
Figure 23:
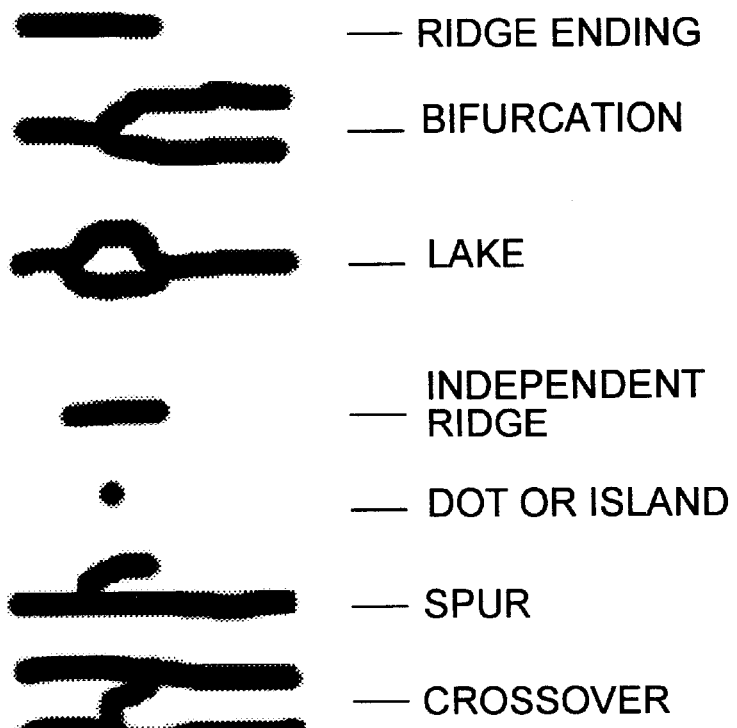
Figure 24:
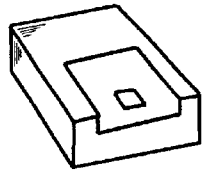
Figure 25:
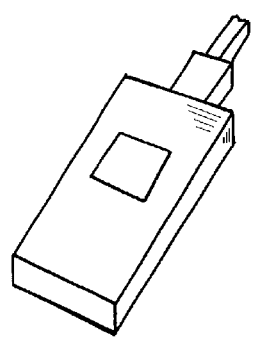
Figure 26:
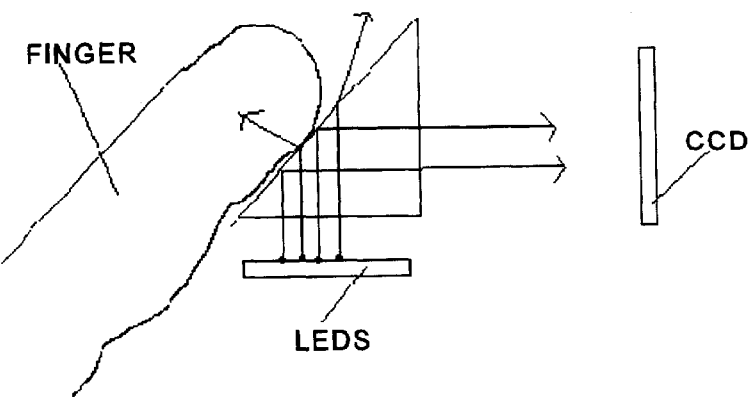
Figure 27:
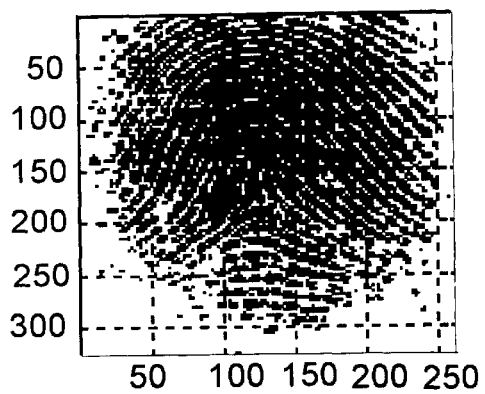
Figure 28:
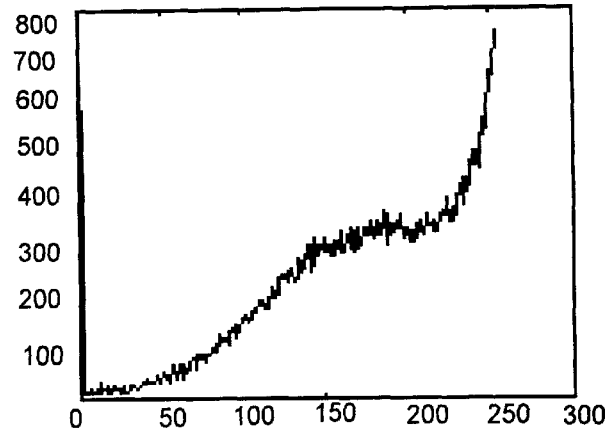
Figure 29:
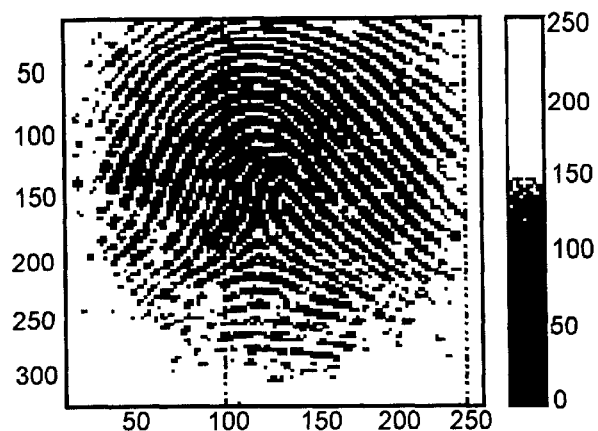
Figure 40:
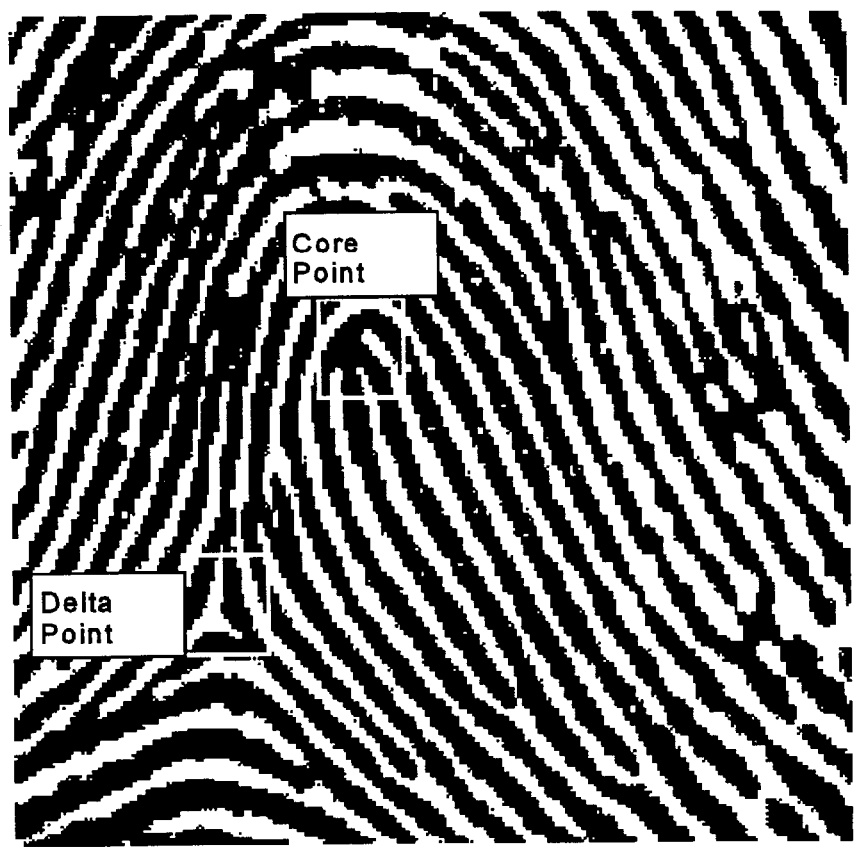
Figure 41:
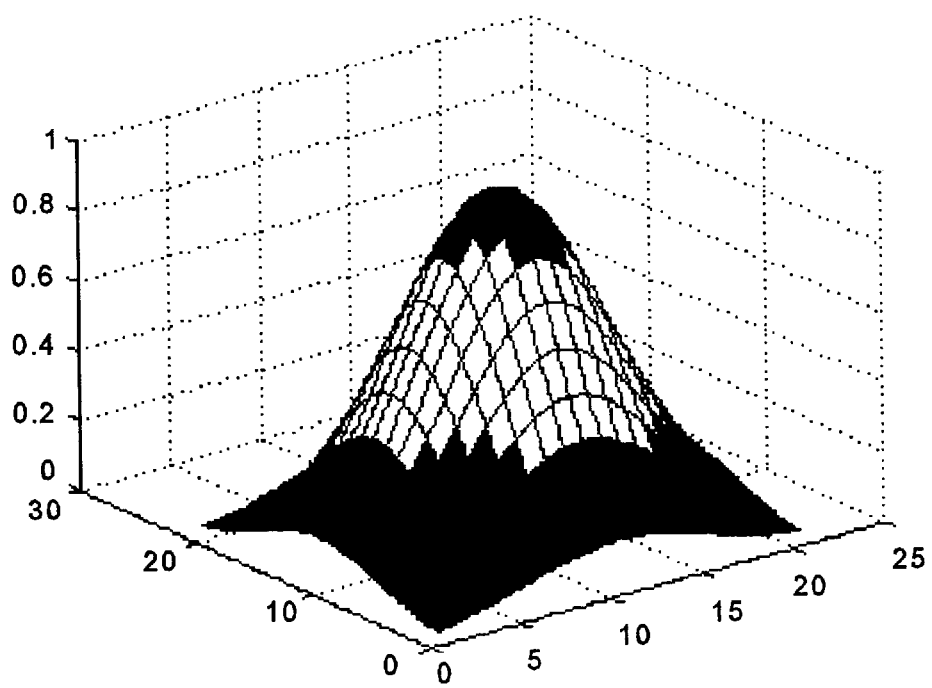
Figure 42:
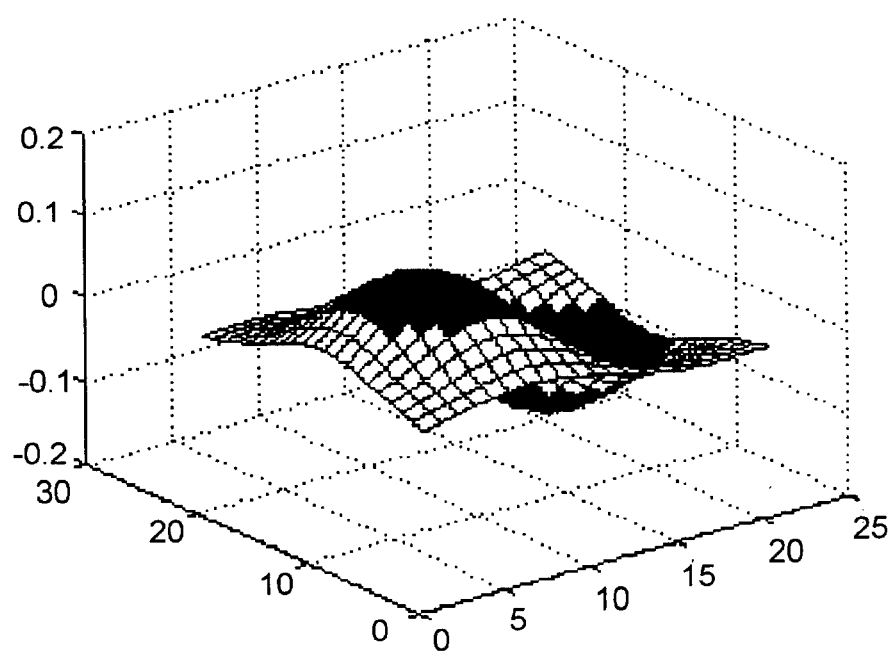
Figure 43:
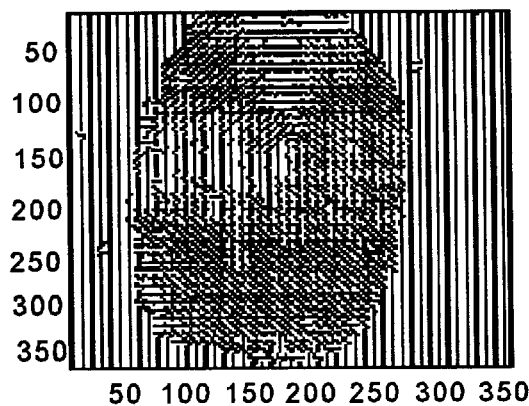
Figure 44:
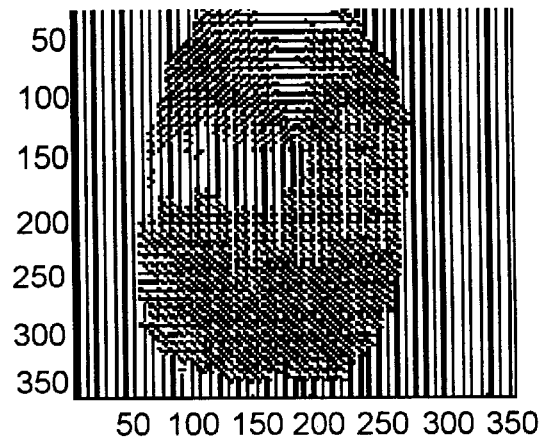
Figure 49:
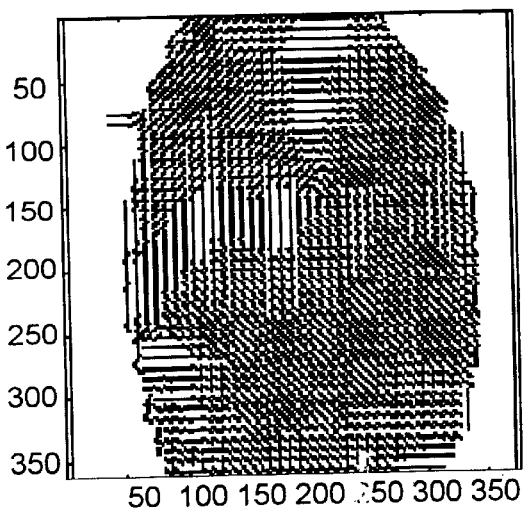
Figure 50:
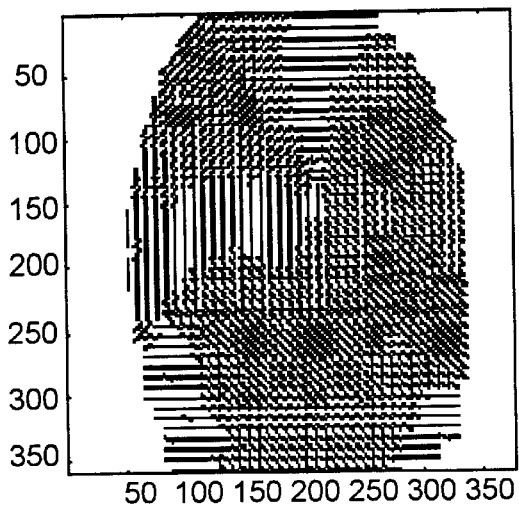
Figure 51:
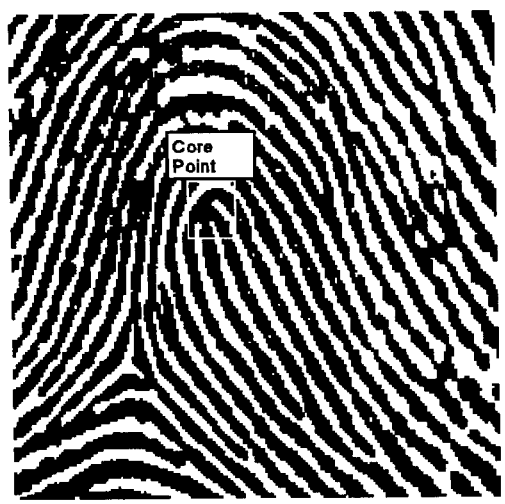
Figure 52:
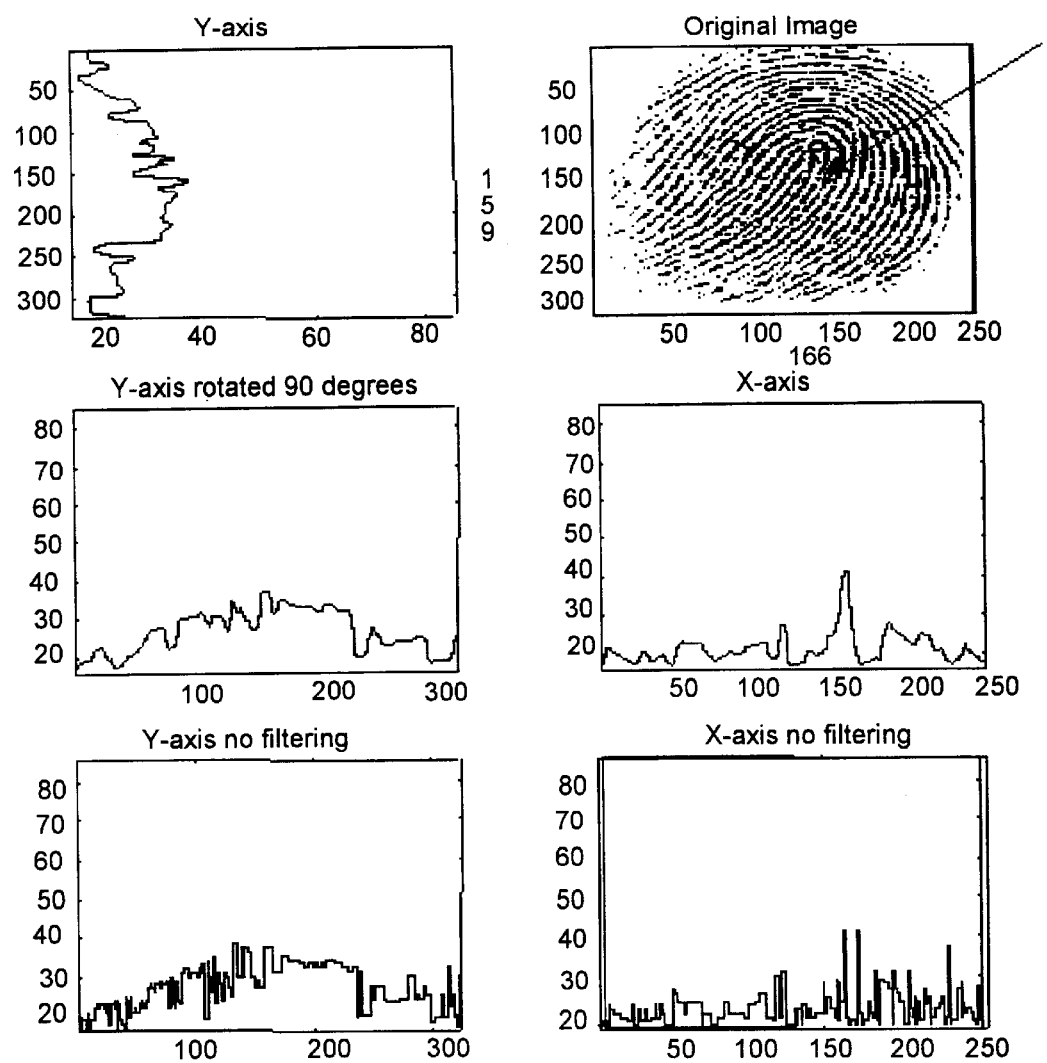
Figure 53:
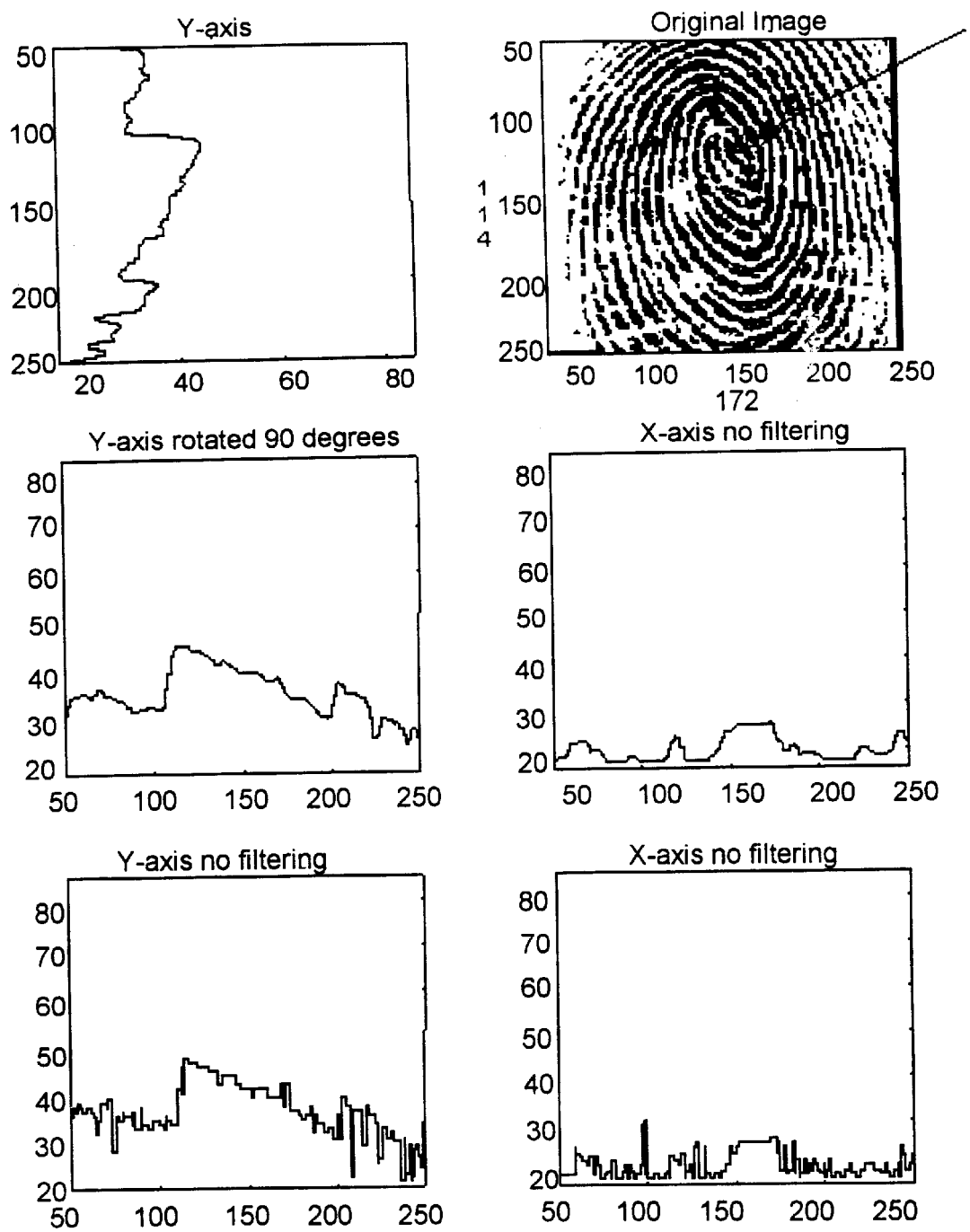
Figure 54:
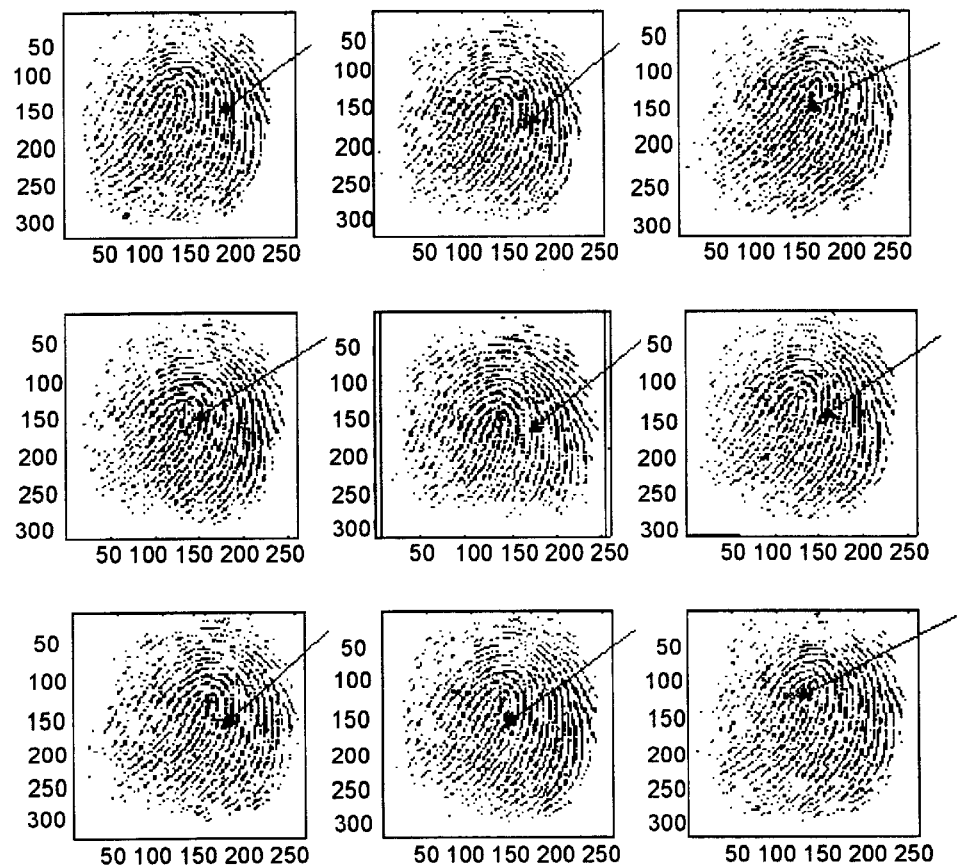
Figure 55:
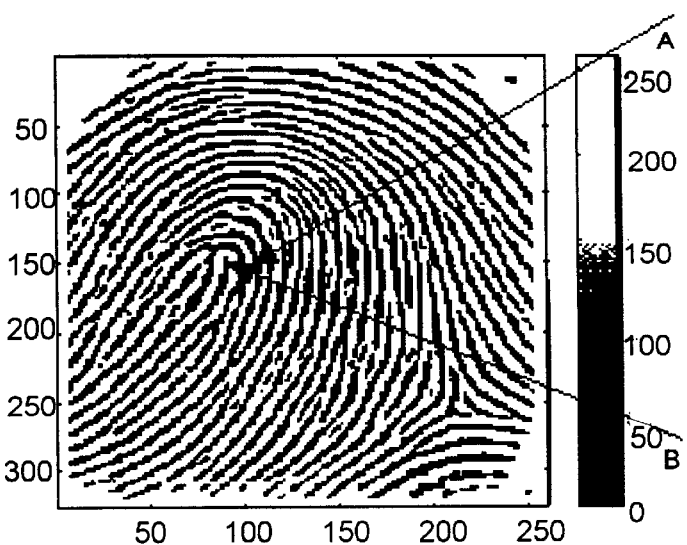
Figure 56:
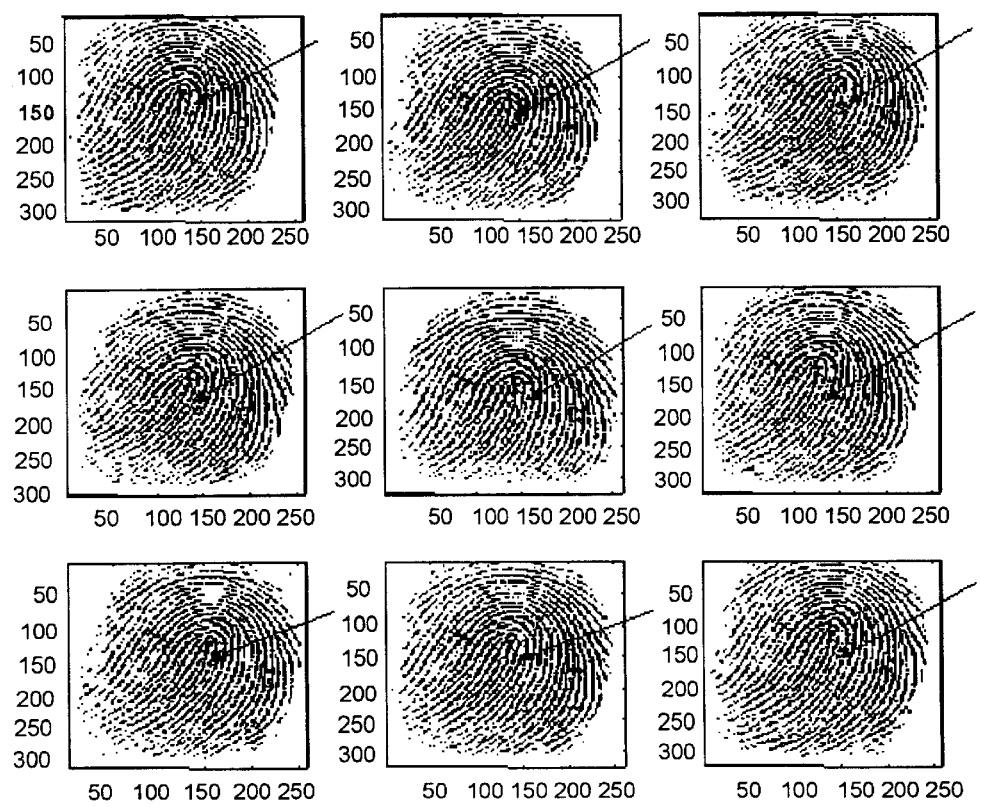
Figure 57:
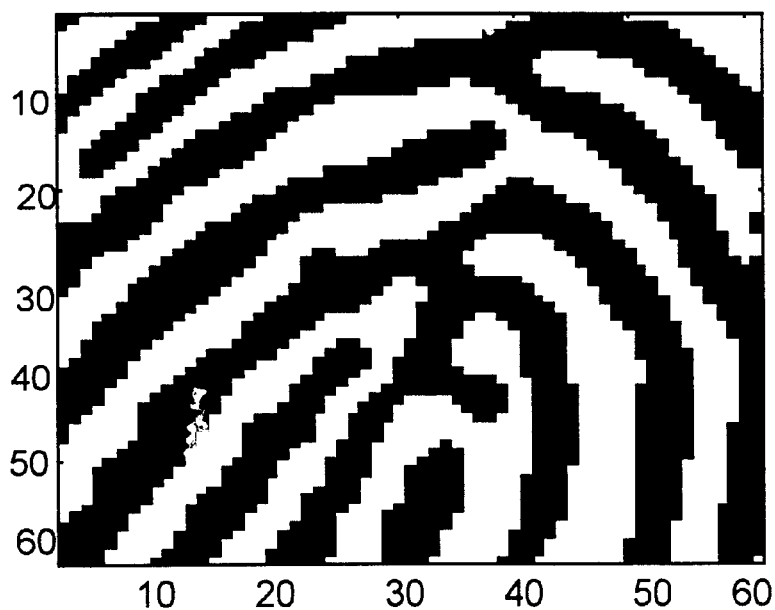
Figure 58:
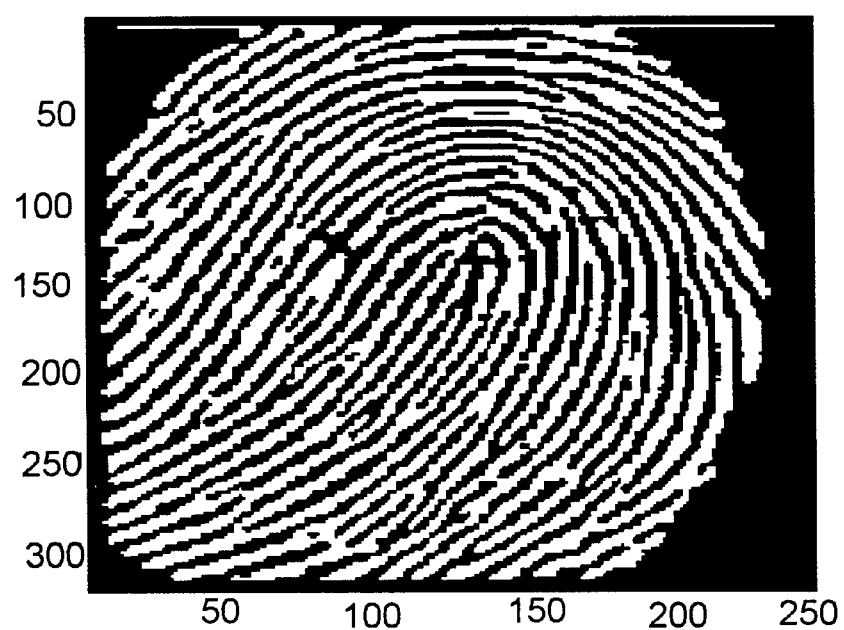
Figure 59:
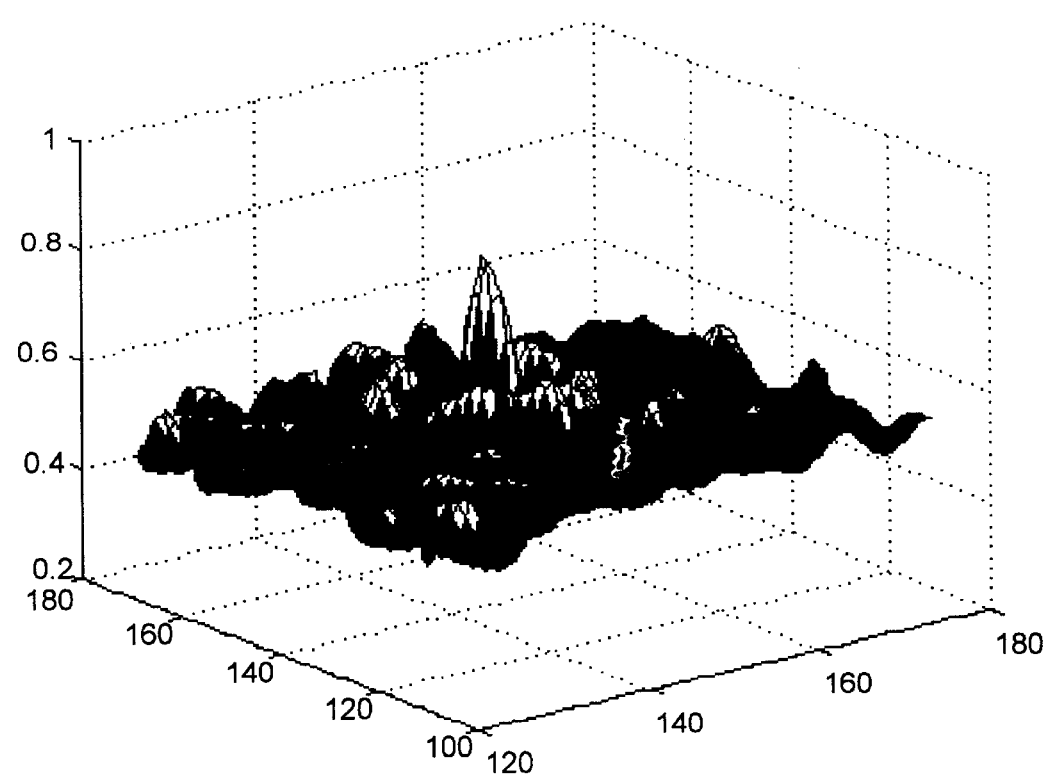
Figure 60:
Figure 61:
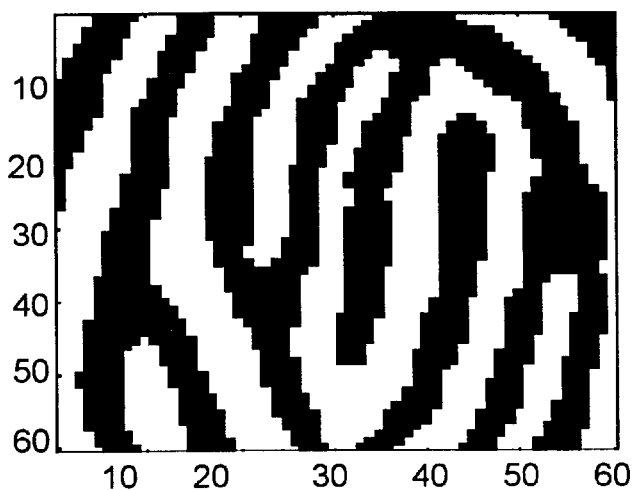
Figure 62:
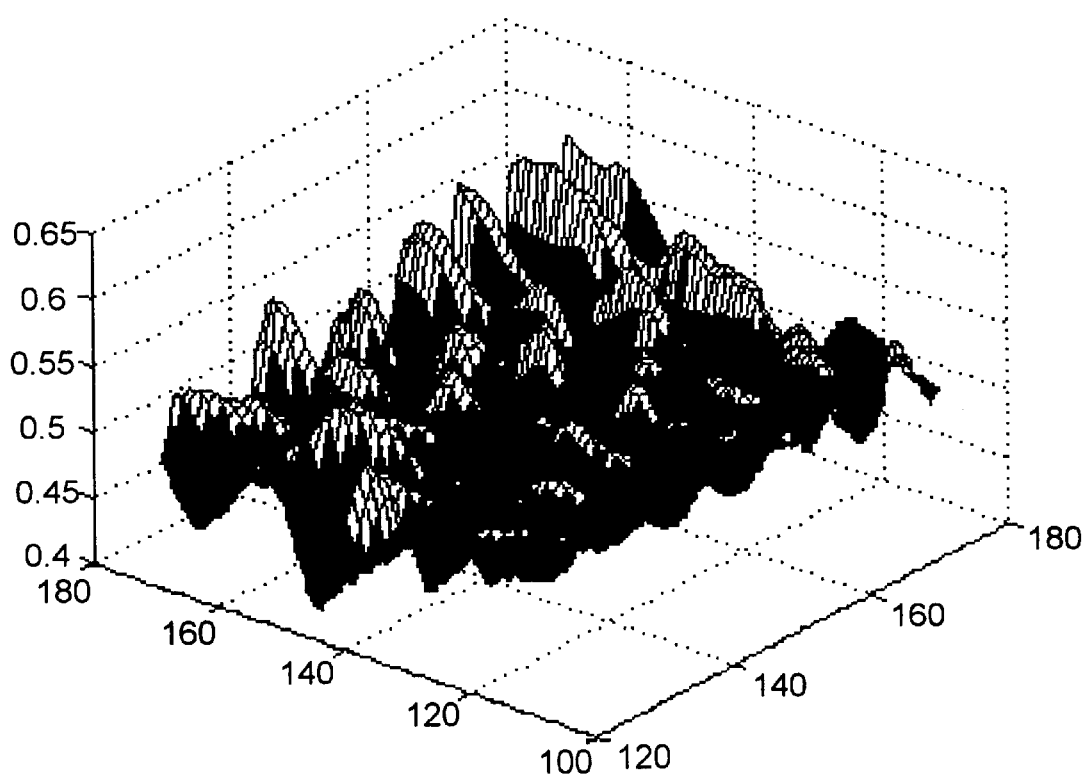
Figure 63:
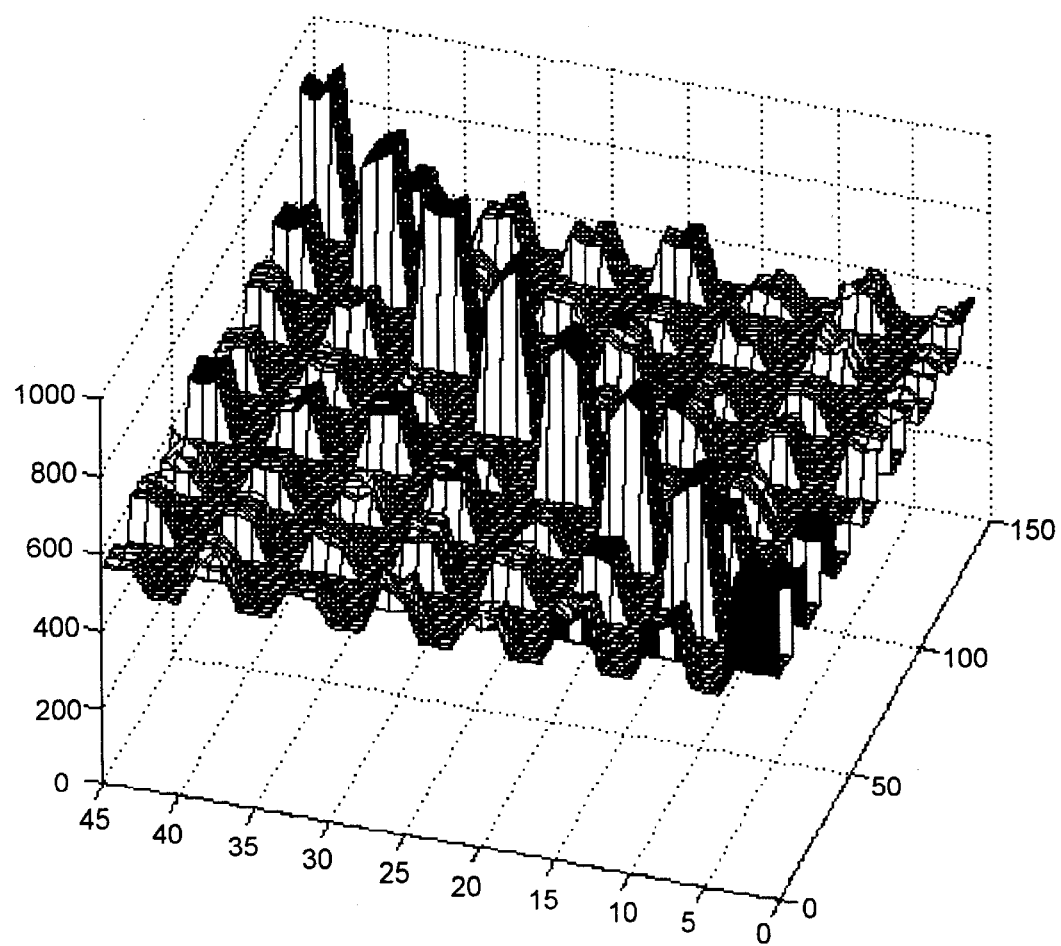

For a real fingerprint, as the images 1410 are acquired, the foreground 1420 of each image becomes progressively larger relative to the previous image so that the foreground covers more and more of the sensor area. This increasing coverage follows from the finger being pressed harder and harder against the sensor. FIG. 15 illustrates this process. If a paper copy of a fingerprint is presented the foreground does not gradually increase in size. Instead, with a paper copy, the foreground, which contains the fingerprint structures, instantly occupies a constant percentage of the sensor area. Similarly, the foreground of a fake fingerprint does not necessarily increase in size at the same rate as a real fingerprint. Also, during the first couple of hundreds of milliseconds, the darkness of the image gradually increases as the pressure of the fingertip against the sensor increases. Accordingly, by measuring this change in the median pixel values of the foreground, a distinction can be made between a fake fingerprint and a real fingerprint.

Additionally, when a person places a finger on the scanner, the finger is never completely still, that is, each successive image differs slightly from the next. Thus, a comparison of the successive images to each other to ensure that none are exactly the same will also indicate that the images being received are from a real fingerprint.

Another use of finger dynamics is to detect the thickness of the ridges as the finger is pressed towards the sensor. As a finger is pressed against a sensor, the ridges appear to thicken because the ridges are 'flattened' against the sensor surface. Additionally, this flattening occurs in a known way. Further, a minute, non-symmetric displacement of the pattern, which can be the result of a small twist or a change of the way of pressing the finger on the sensor is another way of separating real fingerprints from fake fingerprints. Such a difference can be detected by comparing an image with a subsequent one. In both cases, the dynamics of the finger is used as a way to accept real fingerprints and reject counterfeits.

The present invention also encompasses using finger dynamics during image capture for enrollment.

Quality Check 1204: If time permits, a quality check 1204, similar to the quality check 120 for enrollment 100 can be performed on the input candidate image.

Binarization 1208: The candidate image is binarized in the same way as an enrolled image.

Restoration 1210: If time permits, image restoration 1210 similar to the restoration 140 for enrollment 100 can be performed on the input candidate image.

Reference Point Determination 1212: The input reference point 1310 is located in the input candidate binarized image using the same procedure 150 used for the enrolled image.

Input Candidate Center Region Determination 1220: An input center region 1320, in one embodiment, a square have a size of X+m pixels by X+m pixels is selected around the candidate image's reference point 1310. 'X' is the size of the center region stored in the recognition template, and 'm' is selected to be between X divided by 4 (X/4) and 2 multiplied by X (2*X), which for the 48 pixel by 48 pixel example is between 12 and 96.

Center Region Correlation 1230: Correlate the center region of the recognition template with a selected portion of the input candidate center region to determine if these center regions match.

Correlation for this invention is meant in its broadest sense, that is, a pixel-by-pixel comparison between portions of the candidate image information and the stored recognition template information. Correlation at its simplest, means that if a pixel in the image matches a pixel in the template, a fixed value, such as "1", is added to a total. If the pixel in the candidate image does not match the pixel in the recognition template, no addition is made to the total. When each pixel in the candidate image and the recognition template have been checked for matching (compared), the total indicates the amount of correlation between the image and the template. Thus, for example in one embodiment, a match value between 0%, that is zero, and 100%, that is one, is obtained from the correlation. 0% indicates a complete mis-match and 100% indicates a perfect match. Of course, other types of correlation are encompassed by this invention, including: (1) multiplying each pixel in the image by the corresponding pixel in the template and integrating to obtain the correlation; and (2) logically 'XORing' (exclusive OR) each pixel in the image by the corresponding pixel in the template and taking the summation of the results. Thus, if gray-scale images and templates are used instead of a binarized images and templates, correlation can still be performed in accordance with the present invention.

In one embodiment, a threshold value between 0% and 100% is selected to determine an acceptable match ('thresh middle').

If the match is not acceptable, different portions of the input candidate center region are selected and additional correlations are performed. These other portions can be rotationally and/or positionally shifted with respect to each other within the input candidate center region. In one embodiment, rotation steps of between 2 degrees and 5 degrees were found sufficient to achieve acceptable matching values. Thus, the input candidate image could be rotated ±180 degrees or more with respect to the center region of the recognition template. In another embodiment, the results of each correlation is used to determine the selection of the next portion of the input candidate center region to correlate with the center region of the recognition template until a maximum match value for the recognition template center region is identified. The center of that portion of the input candidate center region deemed an acceptable match is selected as the best match reference point 1330.

The center region correlation procedure according to one embodiment of the present invention is discussed below with respect to three scenarios, A, B, and C:

Successive input candidate center region portions within 2D the X+m pixel by X+m pixel area are correlated with the recognition template center region until all the desired portions have been correlated. The desired portions can be rotations and or position shifts relative to the candidate's reference point.

A: If no match is found, 'm' is increased in size, that is, the input candidate center region is enlarged, and additional correlations are performed with the recognition template's center region. If still no match is found, the user is then rejected.

B: If only one input candidate center region portion is successfully matched, that is, has a match value higher than thresh middle, that portion is selected as the best match center region 1350 and the center of this region is selected as the best match reference point 1330.

C: If more than one input candidate center region portion exceeds thresh middle, one of these portions has a significantly higher match value, that portion is selected as the best match center region 1350. However, if several portions have approximately the same match value, each of these portions are selected as best match center regions for subsequent use in this matching procedure 1200.

Outlying Region Correlation 1240: Once one or more best match center regions 1350 are selected, each best match center region can be used as the basis for the outlying region correlations. For each best match center region 1350, the entire input candidate binarized image is rotated to correspond to the rotation for that best match center region. Then, location information 1340 for each of the outlying regions stored in the recognition template is used to locate a respective input candidate outlying region 1360 on the input candidate image. The size of each input candidate outlying region 1360, in one embodiment, is selected to be a square of X+z pixels by X+z pixels, where z is selected be less than m. Then, a similar correlation procedure is performed with respect to the procedure used for the center region correlation, except that the desired portions of each input candidate outlying region 1360 selected are not permitted to vary in rotation or position shift from one to another as much as the center region.

Various match parameters can be set by a system manager. For example, the threshold value for an acceptable match value for the center region and/or an outlying region, the number of outlying regions to correlate, and/or the number of outlying regions achieving an acceptable match value to accept a fingerprint as a match, can be set directly by the system manager. The system manager can also indirectly set these match parameters indirectly by selecting a desired security level, for example, between 1 and 10. For example, in one embodiment, if two outlying regions fail to match, the user is rejected 1250, even if the center region matched.

Depending on the security needs of a particular installation, the number of outlying regions stored in the recognition template can be selected at enrollment. Thus, for example, the recognition template for access to a high security building can include ten outlying regions, whereas for a low security building, perhaps only three outlying regions need be stored in the recognition template.

Acceptance 1260: The user is accepted, that is matched, if the requirements for the selected matching parameters have been satisfied. In one embodiment of the present invention, all but one of the outlying regions compared must match, and a sufficient number, for example, between 3 and 10, of the outlying regions must have been available for correlation. An outlying region may not be available if the input candidate image is of a low quality.

One concern of using bitmaps for fingerprint matching is that if an unauthorized party somehow obtains the stored fingerprint image information, duplicates of the fingerprint, or images thereof, could be reconstructed. However, with the present invention, such reconstruction is impossible because the complete fingerprint bitmap is not stored in the recognition template. Instead, only selected regions of the fingerprint image are stored. Further, in one embodiment of the present invention, the location of these outlying regions, that is, the location information is encoded and/or encrypted.

Identifying an input candidate fingerprint from a database requires more time than verification simply because the input candidate image has to be compared to a larger number of stored images. The way the database is searched is critical to reducing this time. When searching through a database of considerable size some kind of classification system reduces the number of stored fingerprints which have to be compared. Problems in classifying fingerprint images are well known. For example, the traditional classes and subclasses are not fully separable, that is some fingerprints can belong to more than one class. Also, some fingerprints do not fit into any of the classes, for example, fingerprints with scars, defective fingerprints, etc. Additionally, a hierarchical classification is useless unless the classification is 100 percent accurate and no such automated classification scheme is known to exist. Also, in a traditional hierarchical 'tree structure' database, the candidate image is first classified as being a specific type of fingerprint. Further subclassifications are then used within each class to locate a stored matching image. However, with such a hierarchical system, once a class or subclass is selected, further classification is only performed down that 'branch' of the hierarchical tree structure.

Instead, according to one embodiment of the present invention, a non-hierarchical database is used. In this database, certain characteristics of a fingerprint image, for example, the number of ridges crossing a certain line and/or ridge thickness, are numerically represented which permits each fingerprint to be located at a specific location in an N-dimensional space. When later searching in the database the input candidate image is represented using the same numerical representations and the N-dimensional fingerprint space is searched starting from the location of the input candidate fingerprint image in the N-dimensional space. Thus, the search is not limited to a certain branch of a database tree structure. Instead, the entire database can be searched, albeit starting at an initial point in the N-dimensional space from which the likelihood is high that the matching recognition template will be found nearby (quickly). Also, the portion of the database that is searched can be selected depending on different factors such as time, false acceptance ratio (FAR), and/or false rejection ratio (FRR).

Each of the selected image characteristics corresponds to a coordinate of a recognition template's point in N-dimensional space. These coordinates can be stored in the recognition template along with the rest of the recognition template information. When the database is accessed for identification purposes, the coordinates for the input candidate image are calculated and some form of geometric distance between these coordinates and the recognition template coordinates stored in the database is calculated. The distance can be calculated, for example, by using the Pythagorean theorem or N-dimensional octagons (which require less computation). The first recognition template which should be attempted to be matched is the recognition template having coordinates located the shortest distance from those of the input candidate image.

As a specific example, according to one embodiment of the present invention, the N-dimensional space is defined with four dimensions. The template of this embodiment includes a square center region from the binarized image of 100 pixels by 100 pixels centered on the reference point. Along the four lines defining the outer perimeter of the square, the number of transitions from black to white and white to black are counted. These values provide four numbers as coordinates to define a point in 4-dimensional space. The coordinates for this point are stored along with the rest of the information forming the recognition template. When searching the fingerprint space, in this case 4-dimensional space, the distances between points in the 4-dimensional space can be calculated using straight forward Euclidian distances, that is, $d^2=\mathrm{sqrt}((x_i-x_j)^2+(y_i-y_j)^2+(z_i-z_j)^2+(v_i-v_j)^2)$.

Thus, it is apparent that in accordance with the present invention an apparatus and method that fully satisfies the objectives, aims, and advantages is set forth above. While the invention has been described in conjunction with specific embodiments and examples, it is evident that many alternatives, modifications, permutations, and variations will become apparent to those skilled in the art in the light of the foregoing description. Accordingly, it is intended that the present invention embrace all such alternatives, modifications and variations as fall within the scope of the appended claims.

What is claimed is:

1. A fingerprint processing method comprising the steps of:
   obtaining an image of a fingerprint comprising ridges and valleys;
   searching the image to locate a reference point; and
   selecting the reference point and a region in the vicinity of the reference point as a recognition template for the image, the region comprising a portion of the image.

2. The method of claim 1, wherein the obtaining step further comprises the steps of:
   applying the fingerprint to a scanning device;
   scanning the fingerprint to generate an image signal; and
   storing the image signal as a digital image.

3. The method of claim 2, wherein the selecting step further comprises the steps of:
   calculating a geographic center of the digital image; and
   selecting the geographic center as the reference point.

4. The method of claim 1, wherein the searching step comprises the steps of:
   selecting a starting point;
   following along at least one ridge proximate the starting point to locate a ridge of a first type;
   selecting adjacent ridges of the first type along a predetermined path to locate a ridge of a second type; and
   selecting a point on a last located ridge of the first type as the reference point.

5. The method of claim 1, wherein the selecting step comprises the steps of:
   selecting the region to include the reference point, the region having a size and a shape; and
   storing the recognition template.

6. The method of claim 1, wherein the step of selecting the region includes the steps of:
   identifying at least one feature in the image; and
   selecting the region to include the at least one feature.

7. The method of claim 1, wherein the step of selecting the region includes the step of:
   selecting the region to include a particular location relative to the reference point.

8. A computer program stored on a computer readable medium comprising the steps of claim 1.

9. A fingerprint processing method comprising the steps of:
   applying the fingerprint to a scanning device;
   scanning the fingerprint to generate an image signal;
   storing the image signal as a digital image;
   vectorizing the digital image;
   selecting a starting sub-area in the vectorized image;
   scanning from the starting sub-area along an orientation of each subsequent sub-area to locate a first sub-area having a horizontal orientation, the first sub-area included in a first horizontal structure;
   scanning from the first sub-area across acceptable structures and along a path of acceptable sub-areas until an unacceptable sub-area is located;
   selecting a center point of a last acceptable sub-area as the reference point; and
   selecting the reference point and a region in the vicinity of the reference point as a recognition template for the image.

10. A computer program stored on a computer readable medium comprising the steps of claim 9.

11. A fingerprint processing method comprising the steps of:
   applying the fingerprint to a scanning device;
   scanning the fingerprint to generate an image signal;
   storing the image signal as a digital image;
   binarizing the digital image;
   determining which row of the digital image has the greatest number of binary transitions;
   determining which column of the digital image has the greatest number of binary transitions;
   selecting a point in the image by following a path starting from a point in the image having the row and the column as coordinates; and
   selecting the reference point and a region in the vicinity of the reference point as a recognition template for the image.

12. A computer program stored on a computer readable medium comprising the steps of claim 11.

13. A fingerprint processing method comprising the steps of:
   obtaining an image of a fingerprint comprising ridges and valleys;
   searching the image to locate a reference point;
   selecting the reference point and a region in the vicinity of the reference point as part of a recognition template for the image;
   selecting other regions, each of the other regions having a respective size and a respective shape, each such other region located with respect to the reference point according to relative location information;
   selecting the other regions, and the respective relative location information for each respective other region as part of the recognition template for the image; and
   storing the recognition template, the region and the other regions comprising respective portions of the image.

14. A computer program stored on a computer readable medium comprising the steps of claim 13.

15. A fingerprint processing method comprising the steps of:
   obtaining an image of a fingerprint comprising ridges and valleys;
   searching the image to locate a reference point;
   selecting the reference point and a region in the vicinity of the reference point as part of a recognition template for the image;
   selecting other regions, each of the other regions having a respective size and a respective shape, each such other region located with respect to the reference point according to relative location information;

selecting the other regions, and the respective relative location information for each respective other region as part of the recognition template for the image:

encrypting at least one of the region, the other regions, and the relative location information; and storing the recognition template.

16. A fingerprint processing method comprising the steps of:

obtaining an image of a fingerprint comprising ridges and valleys;

searching the image to locate a reference point;

selecting the reference point and a region in the vicinity of the reference point as part of a recognition template for the image;

selecting other regions, each of the other regions having a respective size and a respective shape, each such other region located with respect to the reference point according to relative location information;

selecting the other regions, and the respective relative location information for each respective other region as part of the recognition template for the image;

compressing at least one of the region, the other regions, and the relative location information; and storing the recognition template.

17. A fingerprint matching method comprising the steps of:

obtaining an image of a fingerprint comprising ridges and valleys;

searching the image to locate a reference point;

selecting the reference point and a region in the vicinity of the reference point, the region comprising a portion of the image;

selecting at least one recognition template, each recognition template comprising a template reference point and a template region, the template region comprising a portion of another image;

correlating at least a portion of the region with the template region to generate a correlation result; and determining whether the correlation result exceeds a predetermined matching requirement.

18. The method of claim 17, further comprising the steps of:

obtaining from the recognition template, relative location information of at least one other template region;

selecting another region from the image utilizing the relative location information with respect to the template reference point;

correlating at least a portion of the another region with the other template region to generate a correlation result; and determining whether the correlation result exceeds a predetermined matching requirement.

19. A computer program stored on a computer readable medium comprising the steps of claim 17.

20. A fingerprint processing method comprising the steps of:

obtaining sequential multiple images of a fingerprint comprising ridges and valleys; and determining dynamics of the obtaining step by comparing the multiple images to each other.

21. A method according to claim 20 further comprising the step of:

determining from the dynamics if the fingerprint is real.

22. A computer program stored on a computer readable medium comprising the steps of claim 20.

23. A fingerprint information database organization method comprising the steps of:

obtaining, from each of a plurality of fingerprints, values associated with each of a number of fingerprint characteristics;

assigning each of the values to a respective coordinate, the coordinates defining a point in a dimensional space in which each fingerprint characteristic corresponds to at least one dimension of the dimensional space; and associating information concerning each fingerprint with a respective point.

24. A method according to claim 23, further comprising the step of:

locating information concerning fingerprints based on proximity of points in the dimensional space.

25. The method of claim 23, wherein the characteristics are selected from the group consisting of: a number of ridges crossing a certain line; a ridge thickness; or a number of transitions along a center line.

26. A computer program stored on a computer readable medium comprising the steps of claim 23.

27. A fingerprint processing device comprising:

a sensor for detecting a fingerprint and for generating an image signal corresponding to the fingerprint;

a processor for receiving the image signal and for identifying a reference point and a region in the vicinity of the reference point in an image formed from the image signal, the region comprising a portion of the image; and a storage device for storing information concerning the reference point and the region.

28. A fingerprint processing device according to claim 27, wherein the device further comprises:

a correlator for comparing information received from the storage device and information concerning a corresponding region in the vicinity of a corresponding reference point of a second image.

29. A computer program stored on a computer readable medium comprising the steps of claim 27.

30. A storage template for a fingerprint processing system comprising:

a first region bitmap comprising a portion of an image of a fingerprint;

a reference point location;

outlying region bitmaps comprising respective portions of the image of the fingerprint; and relative location information, the relative location information corresponding to the location of each of the outlying region bitmaps with respect to the reference point location.

31. A computer program stored on a computer readable medium comprising the steps of claim 30.

* * * * *